(12) United States Patent
Komistek

(10) Patent No.: US 8,915,965 B2
(45) Date of Patent: Dec. 23, 2014

(54) ANTERIOR STABILIZED KNEE IMPLANT

(75) Inventor: Richard David Komistek, Knoxville, TN (US)

(73) Assignee: Depuy (Ireland), Cork (IE)

( * ) Notice: Subject to any disclaimer, the term of this patent is extended or adjusted under 35 U.S.C. 154(b) by 416 days.

(21) Appl. No.: 12/437,000

(22) Filed: May 7, 2009

(65) Prior Publication Data

US 2010/0286788 A1 Nov. 11, 2010

(51) Int. Cl.
*A61F 2/38* (2006.01)

(52) U.S. Cl.
CPC ............. *A61F 2/3886* (2013.01); *A61F 2/3868* (2013.01)
USPC ...................................... 623/20.15

(58) Field of Classification Search
CPC ..... A61F 2/389; A61F 2/3836; A61F 2/3859; A61F 2/3886
USPC .......................... 623/20.14–20.36
See application file for complete search history.

(56) References Cited

U.S. PATENT DOCUMENTS

| | | | |
|---|---|---|---|
| 3,765,033 A | 10/1973 | Goldberg | |
| 3,869,731 A | 3/1975 | Waugh | |
| 4,209,861 A * | 7/1980 | Walker et al. | 623/20.27 |
| 4,215,439 A | 8/1980 | Gold et al. | |
| 4,262,368 A | 4/1981 | Lacey | |
| 4,340,978 A | 7/1982 | Buechel et al. | |
| 4,470,158 A | 9/1984 | Pappas | |
| 4,888,021 A | 12/1989 | Forte et al. | |
| 5,007,933 A | 4/1991 | Sidebotham | |
| 5,071,438 A | 12/1991 | Jones et al. | |
| 5,133,758 A | 7/1992 | Hollister | |
| 5,147,405 A | 9/1992 | Van Zile | |
| 5,219,362 A | 6/1993 | Tuke et al. | |
| 5,326,361 A | 7/1994 | Hollister | |
| 5,330,533 A | 7/1994 | Walker et al. | |
| 5,344,460 A | 9/1994 | Turanyi et al. | |
| 5,358,527 A | 10/1994 | Forte | |
| 5,370,699 A | 12/1994 | Hood | |
| 5,387,240 A | 2/1995 | Pottenger et al. | |

(Continued)

FOREIGN PATENT DOCUMENTS

DE 19529824 A1 2/1997
EP 0636352 2/1995

(Continued)

OTHER PUBLICATIONS

European Search Report From Corresponding EPO App. No. 12164381.1-2310, Dated May 18, 2012, 4 Pages.

(Continued)

*Primary Examiner* — David Isabella
*Assistant Examiner* — Ann Schillinger

(57) ABSTRACT

A posterior cruciate ligament retaining knee implant prosthesis comprising a femoral component including a medial condyle and a lateral condyle separated from one another by an intercondylar channel adapted to accommodate throughput of a native cruciate ligament, both the medial condyle and the lateral condyle posteriorly terminate individually, the medial condyle including a medial condyle bearing surface and the lateral condyle including a lateral condyle bearing surface, the femoral component including an anterior cam, and a tibial component including a medial condyle receiver having a medial condyle receiver bearing surface, the tibial component also including a lateral condyle receiver having a lateral condyle receiver bearing surface, the tibial component also including an anterior post.

53 Claims, 18 Drawing Sheets

(56) References Cited

U.S. PATENT DOCUMENTS

| | | |
|---|---|---|
| 5,395,401 A | 3/1995 | Bahler |
| 5,405,396 A | 4/1995 | Heldreth et al. |
| 5,413,604 A | 5/1995 | Hodge |
| 5,549,686 A | 8/1996 | Johnson et al. |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,658,342 A | 8/1997 | Draganich et al. |
| 5,681,354 A | 10/1997 | Eckhoff |
| 5,683,468 A | 11/1997 | Pappas |
| 5,702,458 A | 12/1997 | Burstein |
| 5,702,466 A | 12/1997 | Pappas et al. |
| 5,755,801 A | 5/1998 | Walker et al. |
| 5,776,201 A | 7/1998 | Colleran et al. |
| 5,778,537 A | 7/1998 | Leini |
| 5,800,552 A | 9/1998 | Forte |
| 5,811,543 A | 9/1998 | Hao |
| 5,824,100 A | 10/1998 | Kester |
| 5,824,102 A | 10/1998 | Buscayret |
| 5,871,543 A | 2/1999 | Hofmann |
| 5,871,546 A | 2/1999 | Colleran et al. |
| 5,935,173 A | 8/1999 | Roger |
| 5,997,577 A | 12/1999 | Herrington |
| 6,004,351 A | 12/1999 | Tomita |
| 6,013,103 A * | 1/2000 | Kaufman et al. .......... 623/20.15 |
| 6,039,764 A | 3/2000 | Pottenger et al. |
| 6,056,779 A | 5/2000 | Noyer et al. |
| 6,080,195 A | 6/2000 | Colleran |
| 6,123,729 A | 9/2000 | Insall |
| 6,206,926 B1 | 3/2001 | Pappas |
| 6,264,697 B1 | 7/2001 | Walker |
| 6,299,646 B1 | 10/2001 | Chambatt et al. |
| 6,325,828 B1 | 12/2001 | Dennis et al. |
| 6,344,059 B1 | 2/2002 | Krakovits |
| 6,379,388 B1 | 4/2002 | Ensign et al. |
| 6,443,991 B1 | 9/2002 | Running |
| 6,475,241 B2 | 11/2002 | Pappas |
| 6,491,726 B2 | 12/2002 | Pappas |
| 6,540,787 B2 | 4/2003 | Biegun |
| 6,558,426 B1 | 5/2003 | Masini |
| 6,582,469 B1 | 6/2003 | Tornier |
| 6,589,283 B1 | 7/2003 | Metzger et al. |
| 6,730,128 B2 | 5/2004 | Burstein |
| 6,764,516 B2 | 7/2004 | Pappas |
| 6,770,099 B2 | 8/2004 | Andriacchi et al. |
| 6,797,005 B2 | 9/2004 | Pappas |
| 6,846,329 B2 | 1/2005 | McMinn |
| 6,893,388 B2 | 5/2005 | Reising |
| 6,893,467 B1 | 5/2005 | Bercovy |
| 6,916,340 B2 | 7/2005 | Metzger et al. |
| 6,926,738 B2 | 8/2005 | Wyss |
| 6,972,039 B2 | 12/2005 | Metzger |
| 6,986,791 B1 | 1/2006 | Metzger |
| 7,025,788 B2 | 4/2006 | Metzger et al. |
| 7,066,963 B2 | 6/2006 | Naegerl |
| 7,081,137 B1 | 7/2006 | Servidio |
| 7,105,027 B2 | 9/2006 | Lipman |
| 7,160,330 B2 | 1/2007 | Axelson, Jr. |
| 7,261,740 B2 | 8/2007 | Tuttle et al. |
| 7,326,252 B2 | 2/2008 | Otto et al. |
| 7,422,605 B2 | 9/2008 | Burstein et al. |
| 7,572,292 B2 | 8/2009 | Crabtree et al. |
| 7,658,767 B2 | 2/2010 | Wyss |
| 7,678,152 B2 | 3/2010 | Suguro |
| 7,842,093 B2 | 11/2010 | Peters |
| 7,875,081 B2 | 1/2011 | Lipman |
| 2003/0009232 A1 | 1/2003 | Metzger |
| 2004/0243244 A1 | 12/2004 | Otto et al. |
| 2004/0243245 A1 | 12/2004 | Plumet |
| 2005/0096747 A1 | 5/2005 | Tuttle |
| 2005/0143832 A1 | 6/2005 | Carson |
| 2005/0154472 A1 | 7/2005 | Afriat |
| 2005/0209701 A1 | 9/2005 | Suguro et al. |
| 2006/0015185 A1 | 1/2006 | Chambat et al. |
| 2006/0178749 A1 | 8/2006 | Pendleton et al. |
| 2007/0135926 A1 | 6/2007 | Walker |
| 2008/0021566 A1 | 1/2008 | Peters |
| 2008/0269596 A1 | 10/2008 | Revie |
| 2009/0043396 A1 | 2/2009 | Komistek |
| 2009/0306785 A1 | 12/2009 | Farrar |
| 2009/0319047 A1 | 12/2009 | Walker |
| 2009/0326663 A1 | 12/2009 | Dun |
| 2010/0016977 A1 | 1/2010 | Masini |
| 2010/0036500 A1 | 2/2010 | Heldreth et al. |

FOREIGN PATENT DOCUMENTS

| | | |
|---|---|---|
| EP | 732091 A2 | 9/1996 |
| EP | 1440675 A1 | 7/2004 |
| EP | 1591082 A2 | 11/2005 |
| EP | 1591082 A3 | 11/2005 |
| EP | 1591082 B1 | 9/2009 |
| EP | 1440675 B1 | 8/2010 |
| FR | 2417971 A1 | 9/1979 |
| FR | 2621243 A1 | 4/1989 |
| FR | 2787012 | 7/1998 |
| FR | 2787012 A1 | 6/2000 |
| FR | 2835178 | 1/2002 |
| JP | 8-500992 T | 2/1996 |
| JP | 2004167255 A | 6/2004 |
| WO | WO 02/09624 A1 | 2/2002 |
| WO | WO 2004058108 A1 | 7/2004 |
| WO | WO 2005/072657 A1 | 8/2005 |
| WO | WO 2007/108804 A1 | 9/2007 |
| WO | WO 2007108933 A1 | 9/2007 |
| WO | WO 2007119173 A2 | 10/2007 |
| WO | WO 2007119173 A3 | 12/2007 |

OTHER PUBLICATIONS

Japanese Search Report for Patent Application No. 2009-501393, Dated Oct. 26, 2010, 5 Pages.

European Search Report in EPO App. No. 10162138.1 Dated Aug. 30, 2010, 7 Pages.

European Search Report in EPO App. No. 09164478.1-2310 Dated Oct. 20, 2009, 6 Pages.

European Search Report in EPO App. No. 09164478.1-2310 Dated Apr. 28, 2010, 12 Pages.

PCT Notification of Transmittal of the International Search Report and the Written Opinion of the International Searching Authority or the Declaration, Jun. 5, 2007, 89 Pages.

Australian Search Report for Application No. 2006340364, Dec. 11, 2009, 2 Pages.

The Longitudinal Axis of the Knee and the Role of the Cruciate Ligaments in Controlling Transverse Rotation, James A. Shaw and David G. Murray, J.Bone Joint Surg Am. 1974;56:1603-1609.

PCT Notification Concerning Transmittal of International Preliminary Report for International Application No. PCT/US2006/010431, Oct. 2, 2008, 6 Pages.

PCT Notification of Transmittal of International Search Report & Written Opinion for International Application No. PCT/US2006/010431, Jun. 5, 2007, 8 Pages.

European Search Report From Corresponding EPO App. No. 12181217.6-2310, Dated Jan. 15, 2013, 7 Pages.

Kessler, et al., "Sagittal Curvature of Total Knee Replacements Predicts In Vivo Kinematics," Clinical Biomechanics 22(1): 52-58, 2007.

Wang, et al., "Biomechanical Differences Exhibited During Sit-To-Stand Between Total Knee Arthroplasty Designs of Varying Radii," J Arthroplasty 21(8): 1196-1199, 2006.

Saari, et al., "The Effect of Tibial Insert Design on Rising From a Chair; Motion Analysis After Total Knee Replacement," Clin Biomech 19(9): 951-956, 2004.

Ranawat, "Design May Be Counterproductive for Optimizing Flexion After TKR," Olin Orthop Rel Res 416: 174-176, 2003.

D'Lima, et al., "Quadricepts Moment Arm and Quadriceps Forces After Total Knee Arthroplasty," Clin Orthop Rel Res 393:213-220, 2001.

(56) References Cited

OTHER PUBLICATIONS

Uvehammer, et al., "In Vivo Kinematics of Total Knee Arthroplasty: Flat Compared With Concave Tibial Joint Surface," J Orthop Res 18(6): 856-864, 2000.

Dennis, et al., "In Vivo Anteroposterior Femorotibial Translation of Total Knee Arthroplasty: A Multicenter Analysis," Clin Orthop Rel Rex, 356: 47-57, 1998.

Clary, et al., "Kinematics of Posterior Stabilized and Cruciate Retaining Knee Implants During an In Vitro Deep Knee Bend," 54th Annual Meeting of the Orthopaedic Research Society, Poster No. 1983, Mar. 2008.

Wang, et al., "A Biomechanical Comparison Between the Single-Axis and Multi-Axis Total Knee Arthroplasty Systems for Stand-To-Sit Movement," Clin Biomech 20(4): 428-433, 2005.

Dennis, et al., "Multicenter Determination of In Vivo Kinematics After Total Knee Arthroplasty," Clin. Orthop. Rel. Res., 416, 37-57, 21 Pages, 2003.

Yoshiya et al., "In Vivo Kinematic Comparison of Posterior Cruciate Retaining and Posterior Stabilized Total Knee Arthroplasties Under Passive and Weight-Bearing Conditions," J. Arthroplasty, vol. 20, No. 6, 2005, 7 Pages.

Bertin et al., "In Vivo Determination of Posterior Femoral Rollback for Subjects Having a Nexgen Posterior Cruciate-Retaining Total Knee Arthroplasty," J. Arthroplasty, vol. 17, No. 8, 2002, 9 Pages.

Suggs, et al., "Three Dimensional Tibiofemoral Articular Contact Kinematics of a Cruciate-Retaining Total Knee Arthroplasty," JBJS-AM, vol. 88, No. 2, 2006, 10 Pages.

Dennis, et al., "In Vivo Determination of Normal and Anterior Cruciate Ligament-Deficient Knee Kinematics," J. Biomechanics, 38, 241-253, 2005, 13 Pages.

Li et al., "Anterior Cruciate Ligament Deficiency Alters the In Vivo Motion of the Tibiofemoral Cartilage Contact Points in Both Anteroposterior and Mediolateral Directions," JBJS-AM, vol. 88, No. 8, Aug. 2006, 10 Pages.

Ries, "Effect of ACL Sacrifice, Retention, or Substitution on K After TKA," http://www.orthosupersite, com/view.asp?rid=23134, Aug. 2007, 5 Pages.

Ferris, "Matching Observed Spiral Form Curves to Equations of Spirals in 2-D Images," The First Japanese-Australian Joint Seminar, 7 Pages, 2001.

Goodfellow et al., "The Mechanics of the Knee and Prosthesis Design," The Journal of Bone and Joint Surgery, vol. 60-B, No. 3, 12 Pages, Aug. 1978.

"Vanguard Complete Knee System," Biomet, Available at http://www.biomet.com/patients/vanguard_complete.cfm, Downloaded on Feb. 2009, 3 Pages.

"Nexgen Complete Knee Solution Cruciate Retaining Knee (CR)," Zimmer, Available at http://zimmer.com.au/ctl?template=pc&op=global&action=&template=pc&id-356, Downloaded on Feb. 18, 2009, 1 Page.

Scorpio Knee TS Single Axis Revision Knee System, Stryker Orthopaedics, http://www.stryker.com/stellent/groups/public/documents/web_prod/023609.pdf, 6 Pages, Literature No. LSKTS/B, 2004.

P. Johal et al., "Tibio-Femoral Movement in the Living Knee. A Study of Weight Bearing and Non-Weight Bearing Knee Kinematics Using 'Interventional' MRI," Journal of Biomechanics, vol. 38, Issue 2, Feb. 2005, pp. 269-276, 8 Pages.

Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, 4 Pages.

Asano et al., "In Vivo Three-Dimensional Knee Kinematics Using a Biplanar Image-Matching Technique," Clin Orthop Rel Res, 388:157-166, 2001, 10 Pages.

EPO Search Report From EPO Patent Application No. 12164381.1-1654, Dated Mar. 7, 2013, 3 Pages.

Barnes, C.L., et al, Kneeling Is Safe for Patients Implanted With Medial-Pivot Total Knee Arthroplasty Designs, Journal of Arthroplasty, vol. 00, No. 0 2010, 1-6, 6 Pages.

Blaha, et al., "Kinematics of the Human Knee Using an Open Chain Cadaver Model", Clinical Orthopaedics and Related Research, vol. 410 (2003); 25-34.

Dennis, et al, "A Multi-Center Analysis of Axial Femorotibial Rotation After Total Knee Arthroplasty", Clinical Orthopaedics 428 (2004): 180-89.

Fan, Cheng-Yu, et al, Primitive Results After Medial-Pivot Knee Arthroplasties: A Minimum 5-Year Follow-Up Study, The Journal of Arthroplasty, vol. 25, No. 3 2010, 492-496, 5 Pages.

Freeman, M.A.R., et al, The Movement of the Normal Tibio-Femoral Joint, The Journal of Biomechanics 38 (2005) (2), pp. 197-208, 12 Pgs.

Fuller, et al., "A Comparison of Lower-Extremity Skeletal Kinematics Measured Using Skin- and Pin-Mounted Markers", Human Movement Science 16 (1997) 219-242.

Hill, et al., "Tibiofemoral Movement 2: The Loaded and Unloaded Living Knee Studied by MRI", The Journal of Bone & Joint Surgery, vol. 82-B, No. 8 (Nov. 2000), 1196-1198.

Karachalios, et al., "A Mid-Term Clinical Outcome Study of the Advance Medial Pivot Knee Arthroplasty," www.sciencedirect.com, The Knee 16 (209); 484-488, 2009.

Komistek, et al., "In Vivo Fluoroscopic Analysis of the Normal Human Knee", Clinical Orthopaecis 410 (2003): 69-81.

Komistek, et al., "In Vivo Polyethylene Bearing Mobility Is Maintained in Posterior Stabilized Total Knee Arthroplasty", Clinical Orthopaedics 428 (2004): 207-213.

Koo, et al., "The Knee Joint Center of Rotation Is Predominantly on the Lateral Side During Normal Walking", Journal of Biomechanics, vol. 41 (2008): 1269-1273.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756.

Moonot, et al., "Correlation Between the Oxford Knee and American Knee Society Scores at Mid-Term Follow-Up", The Journal of Knee Surgery, vol. 22, No. 3 (Jul. 2009), 226-230.

Murphy, Michael Charles, "*Geometry and the Kinematics of the Normal Human Knee*", Submitted to Massachusetts Institute of Technology (1990).

Nakagawa, et al., "Tibiofemoral Movement 3: Full Flexion in the Living Knee Studied by MRI", *The Journal of Bone and Joint Surgery*, vol. 82-B, No. 8 (Nov. 2000): 1199-1200.

Omori, et al., "The Effect of Geometry of the Tibial Polyethylene Insert on the Tibiofemoral Contact Kinematics in Advance Medial Pivot Total Knee Arthroplasty", *The Journal of Orthopaedic Science* (2009) 14:754-760.

Shakespeare, et al., "Flexion After Total Knee Replacement. A Comparison Between the Medial Pivot Knee and a Posterior Stabilised Knee," www.sciencedirect.com, *The Knee 13* (2006): 371-372.

Walker, et al., "Motion of a Mobile Bearing Knee Allowing Translation and Rotation", *Journal of Arthroplasty 17* (2002): 11-19.

European Search Report From EPO App. No. 06739287.8 Dated Mar. 16, 2010, 3 Pages.

Kurosawa, et al., "Geometry and Motion of the Knee for Implant and Orthotic Design", *The Journal of Biomechanics 18* (1985), pp. 487-499, 12 Pages.

\* cited by examiner

ANTERIOR STABILIZED KNEE IMPLANT

RELATED ART

Field of the Invention

The present disclosure relates to orthopedic knee prosthetics and, more specifically, to anterior stabilized orthopedic knee prosthetics for use with posterior cruciate retaining total knee arthroplasty procedures.

BACKGROUND

The knee is the largest joint in the body. Normal knee function is required to perform most everyday activities. The knee is made up of the lower end of the femur, which rotates on the upper end of the tibia, and the patella, which slides in a groove on the end of the femur. Large ligaments attach to the femur and tibia to provide stability. The long thigh muscles give the knee strength.

The joint surfaces where these three bones touch are covered with articular cartilage, a smooth substance that cushions the bones and enables them to move easily. The condition of this cartilage lining the knee joint is a key aspect of normal knee function and is important to the physician when evaluating a potential need for a knee joint replacement.

All remaining surfaces of the knee are covered by a thin, smooth tissue liner called the synovial membrane. This membrane releases a special fluid that lubricates the knee, reducing friction to nearly zero in a healthy knee.

Normally, all of these components work in harmony. But disease or injury can disrupt this harmony, resulting in pain, muscle weakness, and reduced function.

In addition to the smooth cartilage lining on the joint surfaces, there are two smooth discs of cartilage that cushion the space between the bone ends. The inner disc is called the medial meniscus, while the disc on the outer side of the knee joint is called the lateral meniscus. The role of the menisci is to increase the conformity of the joint between the femur and the tibia. The menisci also play an important function as joint shock absorbers by distributing weight-bearing forces, and in reducing friction between the joint segments.

There are also four major ligaments that play an important part in stability of the knee joint. The Medial Collateral Ligament (MCL) and the Lateral Collateral Ligament (LCL) are located on opposing sides on the outside of the joint. The Anterior Cruciate Ligament (ACL) and the Posterior Cruciate Ligament (PCL) are more centrally located ligaments within the joint. The ACL attaches to the knee end of the Femur, at the back of the joint and passes down through the knee joint to the front of the flat upper surface of the Tibia. It passes across the knee joint in a diagonal direction and with the PCL passing in the opposite direction, forms a cross shape, hence the name cruciate ligaments.

Total knee replacement (TKR), also referred to as total knee arthroplasty (TKA), is a surgical procedure where worn, diseased, or damaged surfaces of a knee joint are removed and replaced with artificial surfaces. Materials used for resurfacing of the joint are not only strong and durable but also optimal for joint function as they produce as little friction as possible.

The "artificial joint or prosthesis" generally has three components: (1) a distal femoral component usually made of a biocompatible material such as metal alloys of cobalt-chrome or titanium; (2) a proximal tibial component also made of cobalt chrome or titanium alloy; and a bearing component disposed there between usually formed of a plastic material like polyethylene.

In total knee arthroplasty (TKA) there are three main types of implants: The first main type is the posterior cruciate retaining (PCR) total knee arthroplasty, where the surgeon retains the posterior cruciate ligament and sacrifices the anterior cruciate ligament. The second main type is the posterior stabilizing (PS) total knee arthroplasty, where the surgeon sacrifices both the anterior cruciate ligament (ACL) and the posterior cruciate ligament (PCL). With a PS TKA posterior stabilization is introduced into the TKA by using a cam/post mechanism. The third main type is the posterior cruciate sacrificing (PCS) TKA where the surgeon sacrifices both the ACL and the PCL, but does not use a cam/post mechanism for posterior stabilization. Rather, this TKA type uses constraint in the polyethylene to stabilize the anteroposterior movement.

Any of the above three main types of TKA implant can have a fixed bearing (FB) design or a mobile bearing (MB) design. With the fixed bearing design, the polyethylene insert is either compression molded or fixed in the tibial tray using a locking mechanism. In a mobile bearing design, the polyethylene insert is free to either rotate, translate or both rotate and translate.

While knee arthroplasty is known as one of the most consistently successful surgeries offered, there is room for improvement. For example, the ACL is sacrificed during the installation of a total knee arthroplasty system, and doing so can have a negative clinical impact for some patients.

The role of the ACL is to pull the femur in the anterior direction at terminal extension and at full extension. The ACL, attached to the lateral condyle of the femur also works as a tether and keeps the lateral condyle in contact with the lateral meniscus. The PCL pulls the femur in the posterior direction with increasing flexion. The PCL also acts as a tether on the medical condyle of the femur, keeping the medial condyle in contact with the medial meniscus. Together these two ligaments are vitally important to the stability of the knee joint, especially in contact sports and those that involve fast changes in direction and twisting and pivoting movements. Therefore a torn or absent ACL has serious implications for the stability and function for the knee joint. In other orthopedic fields, surgeons usually recommend ACL replacement surgery for a torn ACL because without the ACL, the femorotibial joint becomes unstable. It is assumed that this instability leads to meniscus and cartilage damage. Unfortunately, the ACL is sacrificed in TKA.

Known TKA implants provide for posterior stabilization, but not anterior stabilization. What is needed, therefore, is a TKA implant that provides for anterior stabilization in the absence of a surgically removed ACL while also accommodating a retained PCL.

INTRODUCTION TO THE INVENTION

Currently, most TKA patients do not receive an implant that replaces the functionality of an absent ACL. Specifically, prior art implants do not resist anterior thrust of the femur relative to the tibia; and such resistance is needed to achieve optimal knee joint functionality.

Referring to FIG. 1, a normal knee joint includes the ACL and PCL. For a normal joint, the ACL is operative to pull the femur anterior while the knee joint is moved toward full extension. Conversely, the PCL is operative to pull the femur posterior while the knee joint is moved toward full flexion. As can be seen in FIG. 1, the normal knee joint proximate full extension demonstrates the femur contacts the anterior aspect of the tibia and the patella is in contact with the femur. This is in stark contrast to the position of the femur and patella in a PCR TKA.

Referring to FIG. 2, a PCR TKA allows the PCL to remain intact and to pull the femur in the posterior direction with flexion, but without the counteracting forces otherwise attributable to the ACL. In a PS TKA, the cam/post mechanisms force the femur in the posterior direction with increasing knee flexion, but from flexion to full extension anterior stabilization does not exist in present day total knee implant. At full extension, the femoral condyle of both PS and PCR TKA contact the tibial insert significantly more posterior than the normal knee, leading to patellar component separation from the femoral component and during activity, the femoral component remains posterior throughout the motion.

The present knee implant system provides for joint motion that more closely mimics the proper function of a natural human knee in part by replacing the function of a healthy anterior cruciate ligament. In one embodiment, the knee implant comprises: a femoral component, the femoral component having a first surface attachable to a femur and a second surface wherein the second surface includes a pair of substantially parallel articular condyles with a slot therebetween, an anterior cam (symmetric, asymmetric, sloped, elongated, round, or variable shapes depending on the angle between the femur and the tibia) extending between the condyles and through the slot; a tibial component attachable to a tibia; and a bearing component disposed between the tibial component and the femoral component, the bearing component having a first surface attached to the tibial component and a second articulating surface that includes two recessed bearing surfaces such that the femoral component is rotatably and slidably engaged with the femoral component condyles, and wherein the bearing surfaces are separated by a spine protruding from between the bearing surfaces and wherein the spine engages with the cam at certain flexion angles of the knee implant such that the spine contacts the cam to force the femoral component in the anterior direction during extension. At full extension, this cam/post engagement will ensure that the femoral condyles contact the tibial insert on the anterior aspect. During flexion the cam will release from the post until engagement no longer exists. Then, the PCL will pull the femur in the posterior direction. The anterior cam/post mechanism will work in unison with the PCL to provide stability to the knee joint. Subjects having an AS TKA will experience an anterior thrust of the femoral component during extension activities, such as chair-rise, stair-climb and during walking.

It is a first aspect of the present invention to provide a total knee implant prosthesis comprising: (a) a posterior retaining ligament femoral component including a pair of condyles interposed by an opening, the femoral component also including an anterior cam; and (b) a posterior retaining ligament tibial component, the tibial component including a post and a pair of condyle depressions.

In a more detailed embodiment of the first aspect, the posterior retaining ligament tibial component includes a tibial tray and a tibial tray insert. In yet another more detailed embodiment, the tibial tray insert is a mobile bearing insert. In a further detailed embodiment, the tibial tray insert is a fixed bearing insert. In still a further detailed embodiment, the tibial tray insert includes the pair of condyle depressions, and the tibial tray includes the post. In a more detailed embodiment, the tibial tray insert includes the pair of condyle depressions, and the tibial tray insert includes the post. In a more detailed embodiment, the post is separable from both the tibial tray insert and the tibial tray. In another more detailed embodiment, the anterior cam is mobile bearing with respect to at least one of the pair of condyles. In still another more detailed embodiment, the anterior cam is fixed bearing with respect to the pair of condyles.

In yet another more detailed embodiment of the first aspect, the tibial tray insert comprises independent pieces, a first independent piece includes a medial condyle depression of the pair of condyle depressions, and a second independent piece includes a lateral condyle depression of the pair of condyle depressions, wherein at least one of the first independent piece and the second independent piece is mobile bearing, with respect to the tibial tray. In still another more detailed embodiment, an anterior surface of the post is planar and substantially vertical. In a further detailed embodiment, an anterior surface of the post is sloped upward from anterior to posterior. In still a further detailed embodiment, an anterior surface of the post is substantially planar and angled to face toward a first of the pair of condyle depressions and away from a second of the pair of condyle depressions. In a more detailed embodiment, an anterior surface of the post includes a helical groove. In a more detailed embodiment, an anterior surface of the post includes a helical projection. In another more detailed embodiment, the helical projection is at least one of symmetrical and asymmetrical. In yet another more detailed embodiment, the helical projection is asymmetrical and a lateral portion of the helical projection protrudes outward on a lateral side more than on a medial side.

In a more detailed embodiment of the first aspect, an anterior surface of the post is sloped upward from posterior to anterior. In yet another more detailed embodiment, an anterior surface of the anterior cam is rounded and substantially perpendicularly oriented with respect to the pair of condyles. In a further detailed embodiment, an anterior surface of the anterior cam is planar and angled to face toward a first of the pair of condyles and away from a second of the pair of condyles. In a more detailed embodiment, an anterior surface of the anterior cam is planar and substantially perpendicularly oriented with respect to the pair of condyles. In a more detailed embodiment, an anterior surface of the anterior cam is rounded and angled to face toward a first of the pair of condyles and away from a second of the pair of condyles. In another more detailed embodiment, an anterior surface includes a projection to be received within the helical groove in the post. In yet another more detailed embodiment, an anterior surface of the anterior cam includes a helical projection. In still another more detailed embodiment, the helical projection is at least one of symmetrical and asymmetrical.

In yet another more detailed embodiment of the first aspect, the helical projection is asymmetrical and a lateral portion of the helical projection protrudes outward on a lateral side more than on a medial side. In still another more detailed embodiment, the post includes a base having a cross-section larger than a cross-section at a top of the post farthest from the tibial tray. In a further detailed embodiment, the tibial tray includes a projection that extends into an area bounded by the tibial tray insert, and the post is mounted to the projection. In still a further detailed embodiment, the post is fixed bearing with respect to the projection. In a more detailed embodiment, post is between 0.125 millimeters and 50 millimeters in length from anterior to posterior. In a more detailed embodiment, post is between 0.125 millimeters and 50 millimeters in width from medial to lateral. In another more detailed embodiment, post is between 0.125 millimeters and 50 millimeters in height from superior to inferior. In yet another more detailed embodiment, the anterior cam is resilient.

In a more detailed embodiment of the first aspect, the anterior cam includes a shock absorber. In yet another more detailed embodiment, the anterior cam includes a spring. In a further detailed embodiment, the anterior cam includes at least two springs, where at least two of the springs have symmetrical spring coefficient. In still a further detailed embodiment, the anterior cam includes at least a medial spring and a lateral spring, where the medial spring and the lateral spring have asymmetrical spring rates. In a more detailed embodiment, a spring rate of the medial spring is lower than a spring rate of the lateral spring. In a more detailed embodiment, the post is resilient. In another more detailed embodiment, the post includes a shock absorber. In yet another more detailed embodiment, the post includes a spring. In still another more detailed embodiment, the post includes at least two springs, where at least two of the springs have symmetrical spring coefficient.

In yet another more detailed embodiment of the first aspect, the post includes at least a medial spring and a lateral spring, where the medial spring and the lateral spring have asymmetrical spring rates. In still another more detailed embodiment, a spring rate of the medial spring is lower than a spring rate of the lateral spring. In a further detailed embodiment, at least one of the tibial tray and the tibial tray insert includes a projection, and the post includes a plurality of cavities, each of the plurality of cavities sized to separately accommodate at least a portion of the projection to secure the post to at least one of the tibial tray and the tibial tray insert. In still a further detailed embodiment, the post includes a projection, and at least one of the tibial tray and the tibial tray insert includes a plurality of cavities, each of the plurality of cavities adapted to house a portion of the projection to secure the post to at least one of the tibial tray and the tibial tray insert. In a more detailed embodiment, the anterior cam is at least one of inset with respect to the medial and lateral condyles, flush with respect to the medial and lateral condyles, and projects outward with respect to the medial and lateral condyles. In a more detailed embodiment, the femoral component includes a projection, and the anterior cam includes a plurality of cavities, each of the plurality of cavities sized to separately accommodate at least a portion of the projection to secure the anterior cam to the femoral component. In another more detailed embodiment, the anterior cam includes a projection, and the femoral component includes a plurality of cavities, each of the plurality of cavities sized to separately accommodate at least a portion of the projection to secure the anterior cam to the femoral component.

It is a second aspect of the present invention to provide a posterior cruciate ligament retaining knee implant prosthesis comprising: (a) a femoral component including a medial condyle and a lateral condyle separated from one another by an intercondylar channel adapted to accommodate throughput of a native cruciate ligament, both the medial condyle and the lateral condyle posteriorly terminate individually, the medial condyle including a medial condyle bearing surface and the lateral condyle including a lateral condyle bearing surface, the femoral component including an anterior post; and (b) a tibial component including a medial condyle receiver having a medial condyle receiver bearing surface, the tibial component also including a lateral condyle receiver having a lateral condyle receiver bearing surface, the tibial component including an anterior cam.

In a more detailed embodiment of the second aspect, the posterior retaining ligament tibial component includes a tibial tray and a tibial tray insert. In yet another more detailed embodiment, the tibial tray insert is a mobile bearing insert. In a further detailed embodiment, the tibial tray insert is a fixed bearing insert. In still a further detailed embodiment, the tibial tray insert includes the pair of condyle depressions, and the tibial tray includes the anterior cam. In a more detailed embodiment, the tibial tray insert includes the pair of condyle depressions, and the tibial tray insert includes the anterior cam. In a more detailed embodiment, the anterior cam is separable from both the tibial tray insert and the tibial tray. In another more detailed embodiment, the post is mobile bearing with respect to at least one of the pair of condyles. In still another more detailed embodiment, the post is fixed bearing with respect to the pair of condyles.

In yet another more detailed embodiment of the second aspect, the tibial tray insert comprises independent pieces, a first independent piece includes a medial condyle depression of the pair of condyle depressions, and a second independent piece includes a lateral condyle depression of the pair of condyle depressions, wherein at least one of the first independent piece and the second independent piece is mobile bearing with respect to the tibial tray. In still another more detailed embodiment, an anterior surface of the post is planar and substantially vertical. In a further detailed embodiment, an anterior surface of the post is sloped upward from anterior to posterior. In still a further detailed embodiment, an anterior surface of the anterior cam is substantially planar and angled to face toward a first of the pair of condyle depressions and away from a second of the pair of condyle depressions. In a more detailed embodiment, an anterior surface of the post includes a helical groove. In a more detailed embodiment, an anterior surface of the post includes a helical projection. In another more detailed embodiment, the helical projection is at least one of symmetrical and asymmetrical. In yet another more detailed embodiment, the helical projection is asymmetrical and a lateral portion of the helical projection protrudes outward on a lateral side more than on a medial side.

In a more detailed embodiment of the second aspect, an anterior surface of the post is sloped upward from posterior to anterior. In yet another more detailed embodiment, an anterior surface of the post is rounded and substantially perpendicularly oriented with respect to the pair of condyles. In a further detailed embodiment, an anterior surface of the post is planar and angled to face toward a first of the pair of condyles and away from a second of the pair of condyles. In a more detailed embodiment, an anterior surface of the post is planar and substantially perpendicularly oriented with respect to the pair of condyles. In a more detailed embodiment, an anterior surface of the post is rounded and angled to face toward a first of the pair of condyles and away from a second of the pair of condyles. In another more detailed embodiment, an anterior surface includes a projection to be received within the helical groove in the anterior cam in yet another more detailed embodiment, an anterior surface of the post includes a helical projection. In still another more detailed embodiment, the helical projection is at least one of symmetrical and asymmetrical.

In yet another more detailed embodiment of the first aspect, the helical projection is asymmetrical and a lateral portion of the helical projection protrudes outward on a lateral side more than on a medial side. In still another more detailed embodiment, the post includes a base having a cross-section larger than a cross-section at a top of the post farthest from the femoral attachment location. In a further detailed embodiment, the tibial tray includes a projection that extends into an area bounded by the tibial tray insert, and the anterior cam is mounted to the projection. In still a further detailed embodiment, the anterior cam is fixed bearing with respect to the projection. In a more detailed embodiment, post is between 0.125 millimeters and 50 millimeters in length from anterior to posterior. In a more detailed embodiment, post is between 0.125 millimeters and 50 millimeters in width from medial to lateral. In another more detailed embodiment, post is between 0.125 millimeters and 50 millimeters in height from superior to inferior. In yet another more detailed embodiment, the anterior cam is resilient.

In a more detailed embodiment of the second aspect, the anterior cam includes a shock absorber. In yet another more detailed embodiment, the anterior cam includes a spring. In a further detailed embodiment, the anterior cam includes at least two springs, where at least two of the springs have symmetrical spring coefficient. In still a further detailed embodiment, the anterior cam includes at least a medial spring and a lateral spring, where the medial spring and the lateral spring have asymmetrical spring rates. In a more detailed embodiment, a spring rate of the medial spring is lower than a spring rate of the lateral spring. In a more detailed embodiment, the post is resilient. In another more detailed embodiment, the post includes a shock absorber. In yet another more detailed embodiment, the post includes a spring. In still another more detailed embodiment, the post includes at least two springs, where at least two of the springs have symmetrical spring coefficient.

In yet another more detailed embodiment of the second aspect, the post includes at least a medial spring and a lateral spring, where the medial spring and the lateral spring have asymmetrical spring rates. In still another more detailed embodiment, a spring rate of the medial spring is lower than a spring rate of the lateral spring. In a further detailed embodiment, at least one of the tibial tray and the tibial tray insert includes a projection, and the anterior cam includes a plurality of cavities, each of the plurality of cavities sized to separately accommodate at least a portion of the projection to secure the anterior cam to at least one of the tibial tray and the tibial tray insert. In still a further detailed embodiment, the anterior cam includes a projection, and at least one of the tibial tray and the tibial tray insert includes a plurality of cavities, each of the plurality of cavities adapted to house a portion of the projection to secure the anterior cam to at least one of the tibial tray and the tibial tray insert. In a more detailed embodiment, the post is at least one of inset with respect to the medial and lateral condyles, flush with respect to the medial and lateral condyles, and projects outward with respect to the medial and lateral condyles. In a more detailed embodiment, the femoral component includes a projection, and the post includes a plurality of cavities, each of the plurality of cavities sized to separately accommodate at least a portion of the projection to secure the post to the femoral component. In another more detailed embodiment, the post includes a projection, and the femoral component includes a plurality of cavities, each of the plurality of cavities sized to separately accommodate at least a portion of the projection to secure the post to the femoral component.

It is a third aspect of the present invention to provide a total knee implant prosthesis comprising: (a) a posterior retaining ligament femoral component including a pair of condyles interposed by an opening to accommodate a posterior cruciate ligament, the femoral component also including an anterior cam; and (b) a posterior retaining ligament tibial component, the tibial component including a post and a pair of condyle depressions, where at least one of the anterior cam and the post is spring biased.

It is a fourth aspect of the present invention to provide a posterior cruciate retaining total knee femoral implant prosthesis comprising a posterior retaining ligament femoral component including a pair of condyles interposed by an opening to accommodate a posterior cruciate ligament, the femoral component also including an anterior cam.

It is a fifth aspect of the present invention to provide a posterior cruciate retaining total knee femoral implant prosthesis comprising a posterior retaining ligament femoral component including a pair of condyles interposed by an opening to accommodate a posterior cruciate ligament, the femoral component also including an anterior post.

It is a sixth aspect of the present invention to provide a posterior cruciate retaining total knee tibial implant prosthesis comprising a posterior retaining ligament tibial component including the tibial component including a cam and a pair of condyle depressions.

It is a seventh aspect of the present invention to provide a posterior cruciate retaining total knee tibial implant prosthesis comprising a posterior retaining ligament tibial component including the tibial component including a cam and a pair of condyle depressions.

It is an eighth aspect of the present invention to provide a total knee implant prosthesis comprising: (a) a posterior retaining ligament femoral component including a pair of condyles interposed by an opening to accommodate a posterior cruciate ligament, the femoral component also including at least one projection extending from at least one of the condyles; and (b) a posterior retaining ligament tibial component, the tibial component including a pair of condyle depressions to receive the pair of condyles, at least one of the pair of condyle depressions includes at least one cavity, each of the at least one cavity adapted to receive one of the at least one projection from the femoral component.

It is a ninth aspect of the present invention to provide a total knee implant prosthesis comprising: (a) a posterior retaining ligament femoral component including a pair of condyles interposed by an opening to accommodate a posterior cruciate ligament, the femoral component also including at least one cavity within at least one of the condyles; and (b) a posterior retaining ligament tibial component, the tibial component including a pair of condyle depressions to receive the pair of condyles, at least one of the pair of condyle depressions includes at least one projection, each of the at least one cavity adapted to receive one of the at least one projection from the tibial component.

It is a tenth aspect of the present invention to provide a total knee implant prosthesis comprising: (a) a posterior retaining ligament femoral component including a medial condyle and a lateral condyle interposed by an opening to accommodate a posterior cruciate ligament, the medial condyle including at least one projection, and the lateral condyle including at least one projection; and (b) a posterior retaining ligament tibial component, the tibial component including a medial condyle receiver and a lateral condyle receiver correspondingly operative to receive the medial and lateral condyles, the medial condyle receiver including at least one cavity to receive the at least one projection of the medial condyle, the lateral condyle receiver including at least one cavity to receive the at least one projection of the lateral condyle.

It is an eleventh aspect of the present invention to provide a total knee implant prosthesis comprising: (a) a posterior retaining ligament femoral component including a medial condyle and a lateral condyle interposed by an opening to accommodate a posterior cruciate ligament, the medial condyle including at least one cavity, and the lateral condyle including at least one cavity; and (b) a posterior retaining ligament tibial component, the tibial component including a medial condyle receiver and a lateral condyle receiver correspondingly operative to receive the medial and lateral condyles, the medial condyle receiver including at least one projection to be received within the at least one cavity of the medial condyle, the lateral condyle receiver including at least one projection to be received within the at least one cavity of the lateral condyle.

DETAILED DESCRIPTION

The exemplary embodiments of the present disclosure are described and illustrated below to encompass prosthetic knee joints and knee joint components, as well as methods of implanting and reconstructing knee joints. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
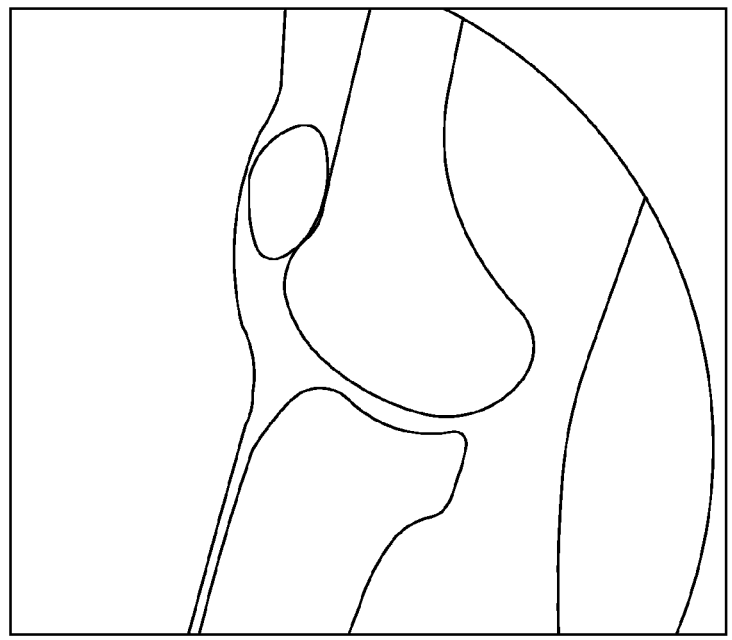
FIG. 1 is an X-ray image of a human knee joint proximate full extension.
Figure 2:
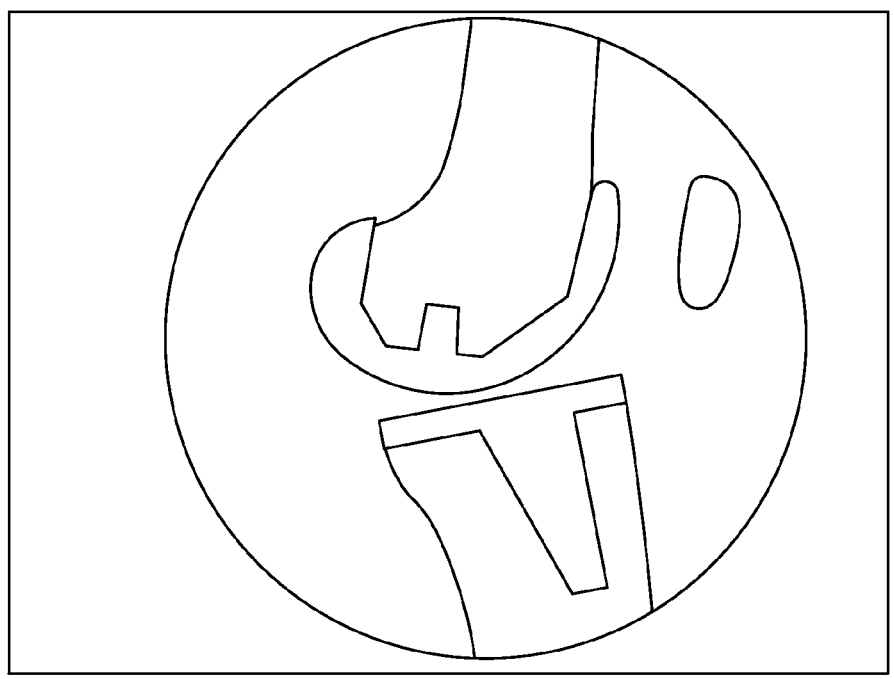
FIG. 2 is an X-ray image of a prosthetic knee joint proximate full extension.

Referencing FIGS. 3A-3D, a series of representations are shown of a generic human anatomy below the torso comprising a femur 10 and a tibia 12 that represent the position of the femur with respect to the tibia as the knee joint 14 flexes. FIG. 1A shows the femur 10 and tibia 12 in axial alignment with respect to a TKA axis 16 when the knee joint 14 is in complete extension. Likewise, FIG. 3A also shows the common position of a femoral component 20 and a tibial component 22 that may be used in a total knee arthroplasty when the prosthetic knee joint is in full extension.

Figures 3A, 3B, 3C, 3D:
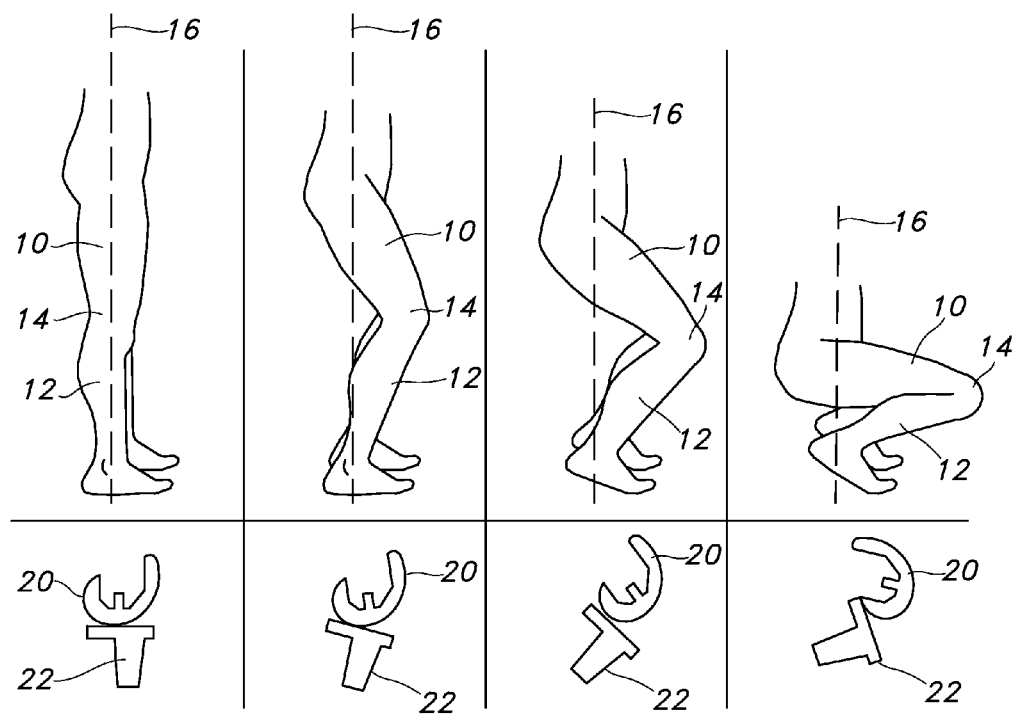
FIGS. 3A-3D are exemplary diagrams showing different degrees of flexion and extension of a natural knee and a corresponding placement of a prosthetic joint when certain flexion or extension occurs.

Referring to FIG. 3B, the knee joint 14 is at approximately 45 degrees of flexion. In this manner, the distal portion of the femur 10 has moved forward relative to the tibia, as has the proximal portion of the tibia 12. Similarly, in the prosthetic knee joint, 45 degrees of flexion causes the tibial component 22 to shift forward with respect to the TKA axis 16 and takes on the angle of the remainder of the tibia. Likewise, the femoral component 20 also shifts forward with respect to the TKA axis 16, but rolls backward (posteriorly) with respect to the tibial component 22 so that a more posterior portion of the condyles of the femoral component are seated within a more posterior portion of the tibial component.

Referencing FIG. 3C, continued flexion of the knee joint 14 to approximately 90 degrees results in further forward motion of the femur 10 and tibia 12 with respect to the TKA axis 16. Consistent with this movement, the femoral component 20 and the tibial component 22 also are moved further forward with respect to the TKA axis 16, but the femoral component continues to rotate posteriorly and move backward on the tibial component.

Referencing FIG. 3D, continued flexion of the knee joint 14 to maximum flexion of approximately 160 degrees results in maximum forward motion of the femur 10 and tibia 12 with respect to the TKA axis 16. Consistent with this movement, the femoral component 20 and the tibial component 22 also are moved further forward with respect to the TKA axis 16 and the femoral component continues to rotate posteriorly and move rearward on the tibial component so that only the most posterior portion of the femoral component 20 remains in contact with the tibial component 22.

Figure 4:
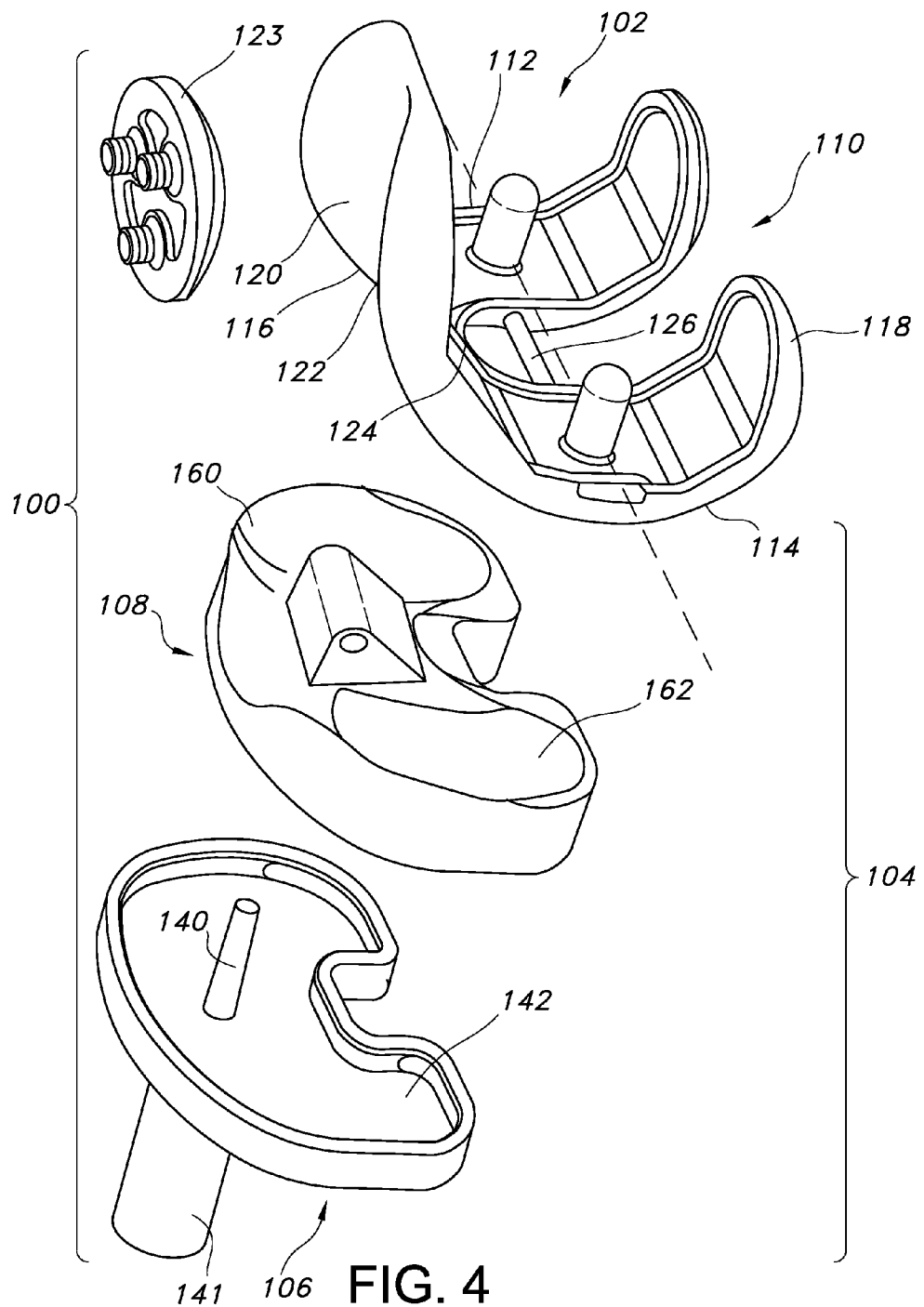
FIG. 4 is an exploded view of a first exemplary embodiment of a posterior cruciate retaining replacement knee providing anterior stabilization.

Referring FIG. 4, an exemplary posterior cruciate retaining orthopedic knee implant 100 for use with total arthroplasty procedures includes a femoral component 102 and a tibial component 104. In this exemplary embodiment, the tibial component 104 comprises a tibial tray 106 and a tibial tray insert 108.

The exemplary posterior cruciate retaining orthopedic femoral component 102 includes a posterior discontinuity or gap 110 between lateral and medial condyles 112, 114 to allow the femoral component to rotate between maximum extension and maximum flexion without impinging the posterior cruciate ligament (PCL), which is retained. In contrast, the anterior cruciate ligament (ACL) is sacrificed or removed during a total arthroplasty procedure. Those skilled in the art are familiar with the posterior constraint resulting from retention of the posterior cruciate ligament, whereas those skilled in the art are also familiar with the absence of anterior constraint resulting from the absence of the anterior cruciate ligament.

This exemplary femoral component 102 includes two condyles 112, 114 each having an arcuate shape in order to allow for smooth rotation of the femur with respect to the tibia. In general, the femoral component includes an anterior portion 116 and a posterior portion 118 that are shown by the dotted line imaginary boundary. The anterior portion 116 includes a front exterior face 120 having a depression 122 adapted to receive at least a portion of a patella component 123. The depression 122 marks the beginning of individual condyle 112, 114 formation. From the top of the front face 120 downward, following the contours of the front face, the curved nature of begins to take shape and transition into individual condyles 112, 114. As the shape of the condyles 112, 114 becomes more pronounced, the condyles separate from one another, which is marked by an arcuate bridge 124 formed at the most proximal connection point of the condyles. As the shape of the condyles 112, 114 continue more distal, past the arcuate bridge 124, the condyles widen and generally flare out on the outer edges. At the same time, the bearing surfaces of the condyles 112, 114 flatten out and do not exhibit a uniform arcuate shape from anterior to posterior. However, the posterior discontinuity or gap 110 has a substantially uniform width, resulting in the inner shape and contour of the condyles being substantially the same. Unlike prior art posterior cruciate retaining femoral components, the exemplary posterior cruciate retaining femoral component 102 includes an anterior cam 126 that engages a post 128 of the tibial component 104.

Figure 5:
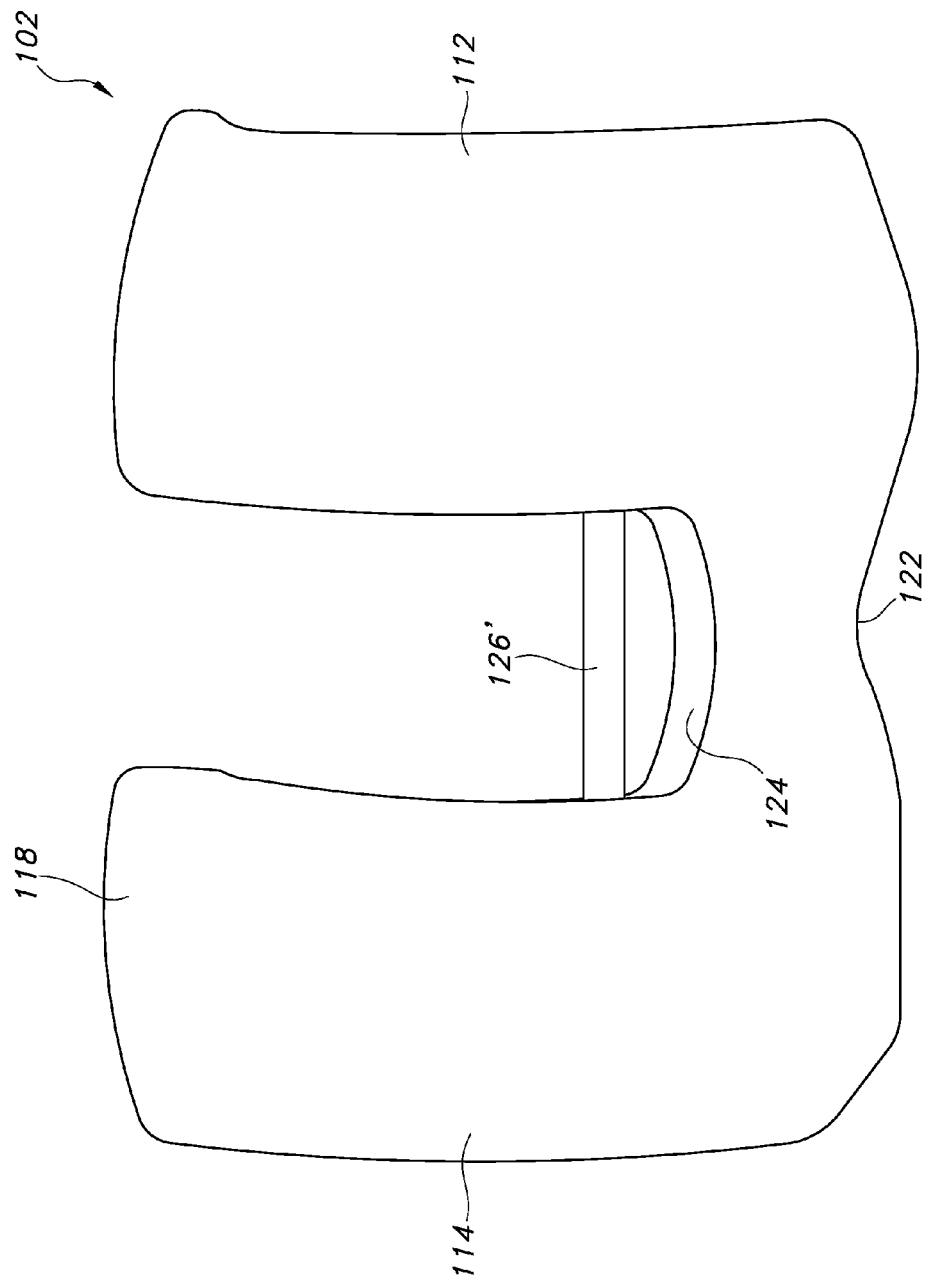
FIG. 5 is a bottom view of an exemplary femoral component in accordance with the present disclosure.

Referring to FIG. 5, the anterior femoral cam 126 of the femoral component 102 may have various shapes. For example, an alternate anterior cam 126' has a camming surface that is arcuate or rounded as a result of the cam having a cylindrical shape. Conversely, the anterior cam 126 could include a camming surface that is substantially flat where the cam is in the shape of a square or rectangular peg.

Figure 6:
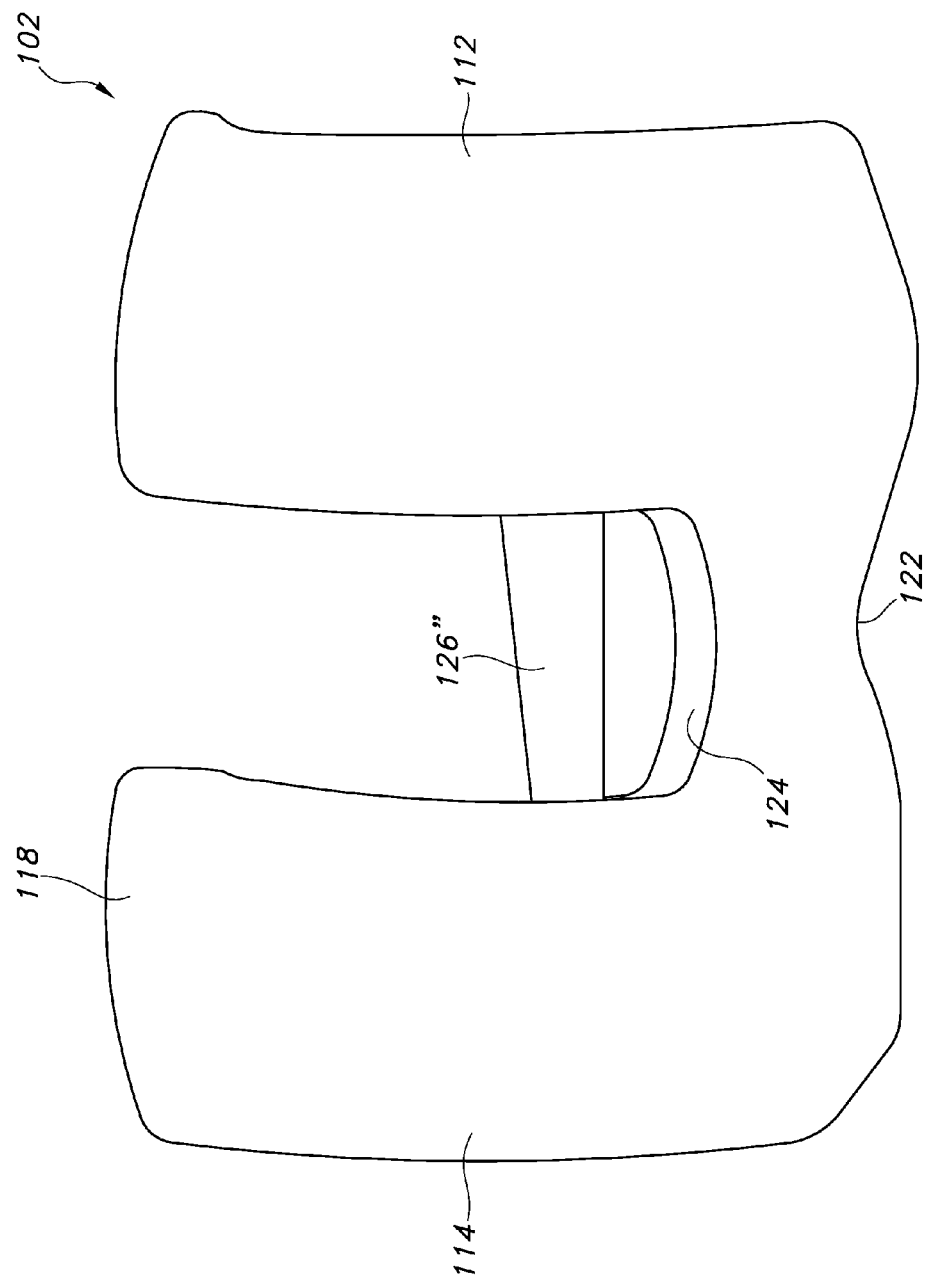
FIG. 6 is a bottom view of another exemplary femoral component in accordance with the present disclosure.

Referring to FIG. 6, in a further alternate exemplary embodiment of the femoral component 102, the anterior cam 126'' has an inclined arcuate or rounded camming surface as a result of the cam having a hybrid shape melding a cylindrical half with a conical half. Because the conical half faces the posterior direction, the conical half comprises the camming surface that interacts with the tibial post 128 (see FIG. 4). In this exemplary embodiment, the camming surface has an inclined slope from the medial condyle 114 to the lateral condyle 112. Conversely, the anterior cam could embody a trapezoidal shape having a substantially flat, but inclined to slope from the medial condyle 114 to the lateral condyle 112.

Figure 7:
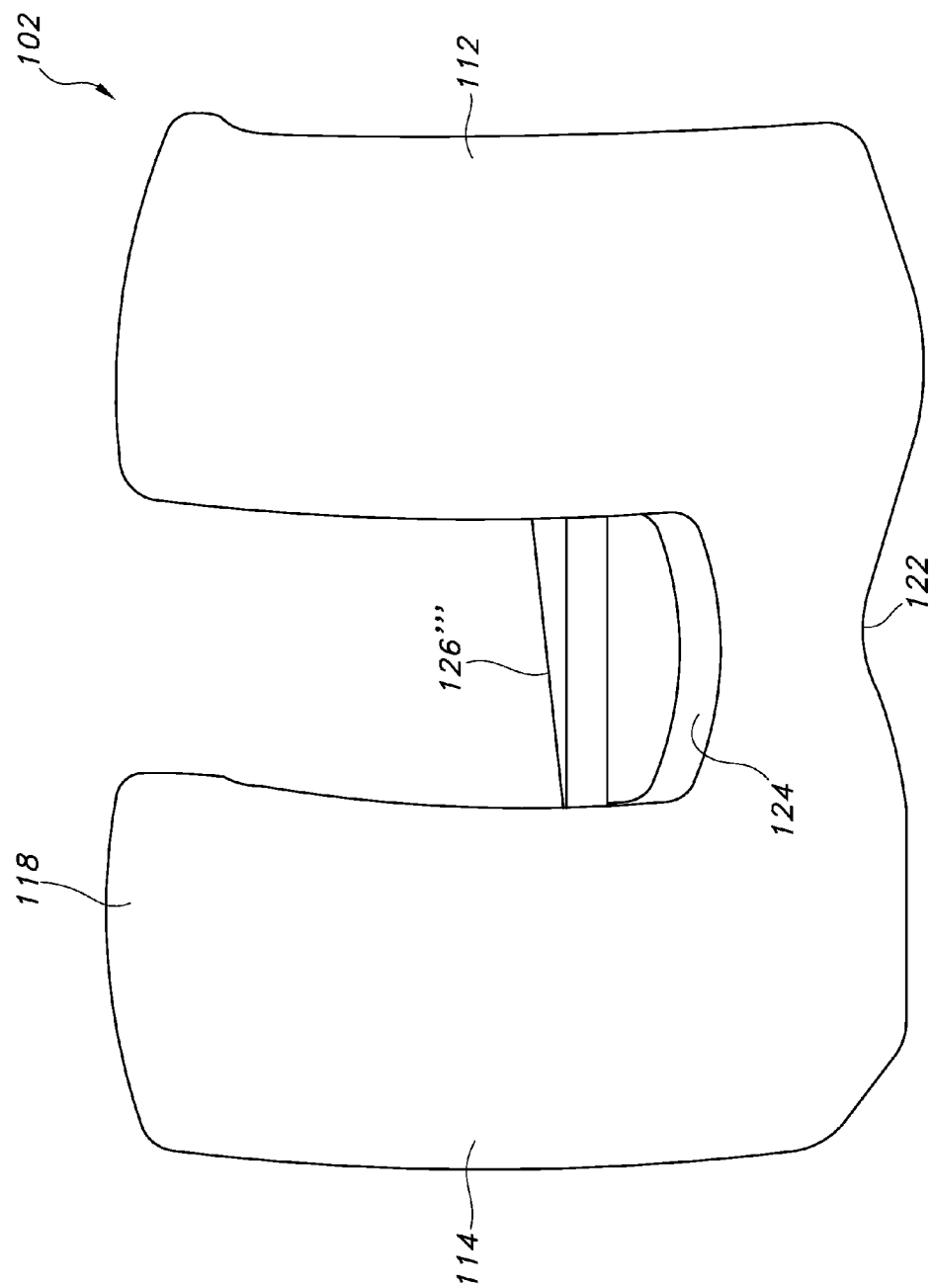
FIG. 7 is a bottom view of a further exemplary femoral component in accordance with the present disclosure.

Referring to FIG. 7, in yet a further alternate exemplary embodiment of the femoral component 102, the anterior cam 126''' has a rounded, helical shape. In other words, the shape of the anterior cam 126''' resembles a worm gear having a helical thread. In this exemplary embodiment, the helical thread increasing in thickness from medial to lateral. Accordingly, as the femoral component is rotated from anterior to posterior, the amount of camming surface contacting the tibial post 128 (see FIG. 4) increases concurrently with increased axial rotation of the femoral component 102.

Figure 8:
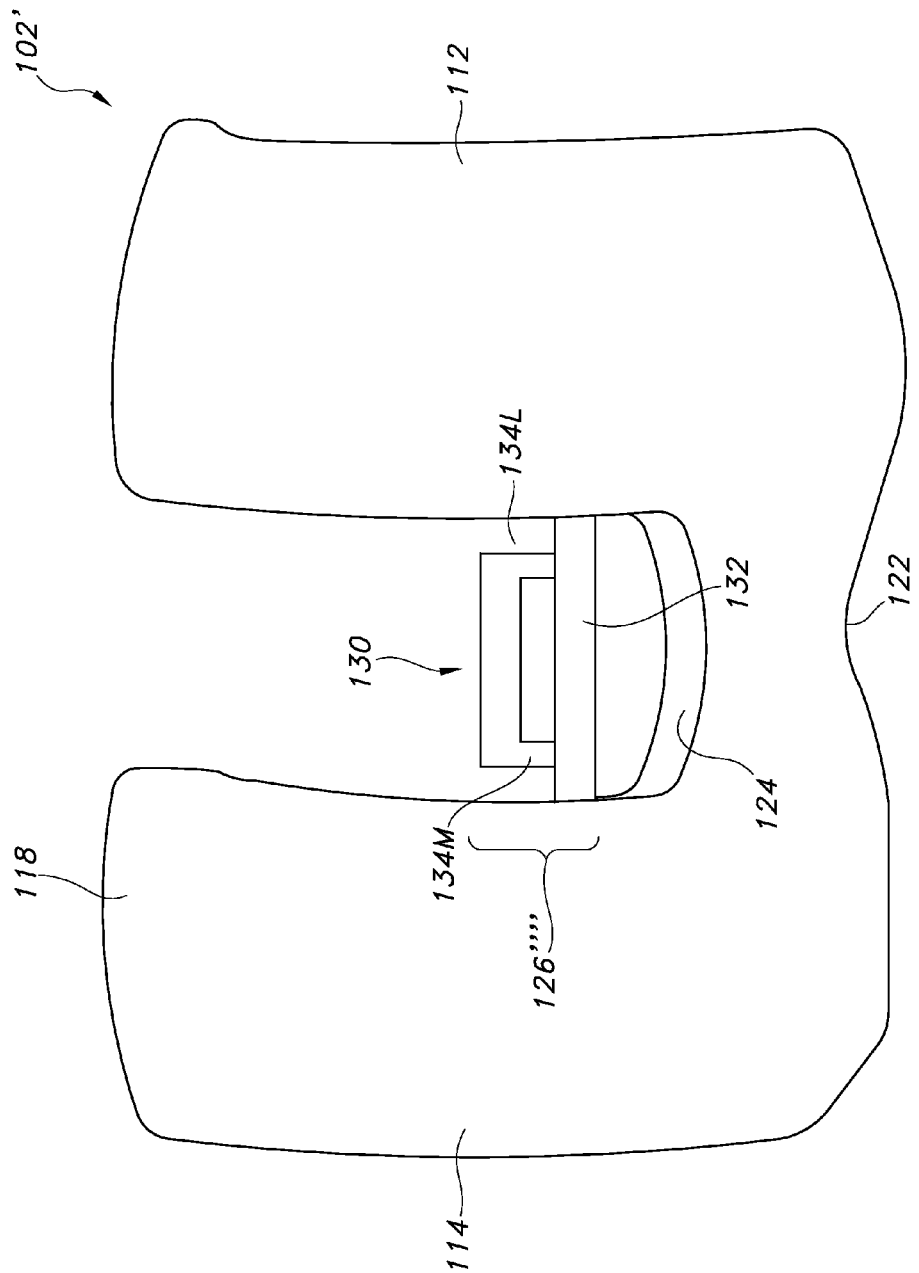
FIG. 8 is a bottom view of yet another exemplary femoral component in accordance with the present disclosure.

Referencing FIG. 8, in still a further alternate exemplary embodiment of the femoral component 102', the anterior cam 126'''' has an arcuate or rounded camming surface that is biased to cushion the impact of the camming surface coming into contact with the tibial post 128 (see FIG. 4). In this alternate exemplary embodiment of the femoral component 102', the camming surface is embodied in a separate component 130 of the anterior cam 126'''' that is mounted to a cam retainer 132, which is mounted to the remainder of the femoral component 102'. A pair of biasing members 134 interposes the camming surface component 130 and the cam retainer. In this exemplary embodiment, each biasing member 134 comprises a helical spring. However, alternate structures may be used in lieu of a helical spring including, without limitation, a resilient bushing or leaf spring.

It is also within the scope of the invention that the medial biasing member 134M and the lateral biasing member 134L having different biasing strengths and/or be comprised of different structures or components. For example, the medial biasing member 134M may comprise a titanium helical spring having a spring rate different than that the lateral biasing member 134L, which comprises a stainless steel leaf spring. In exemplary form, the medial biasing member 134M includes a spring rate substantially less than that of the lateral biasing member 134L so that upon contact with the tibial post 128, the medial biasing member 134M compresses to a greater degree than the lateral biasing member 134L, thus providing a camming surface that is accordingly inclined from the medial condyle 114 to the lateral condyle 112.

Figure 9:
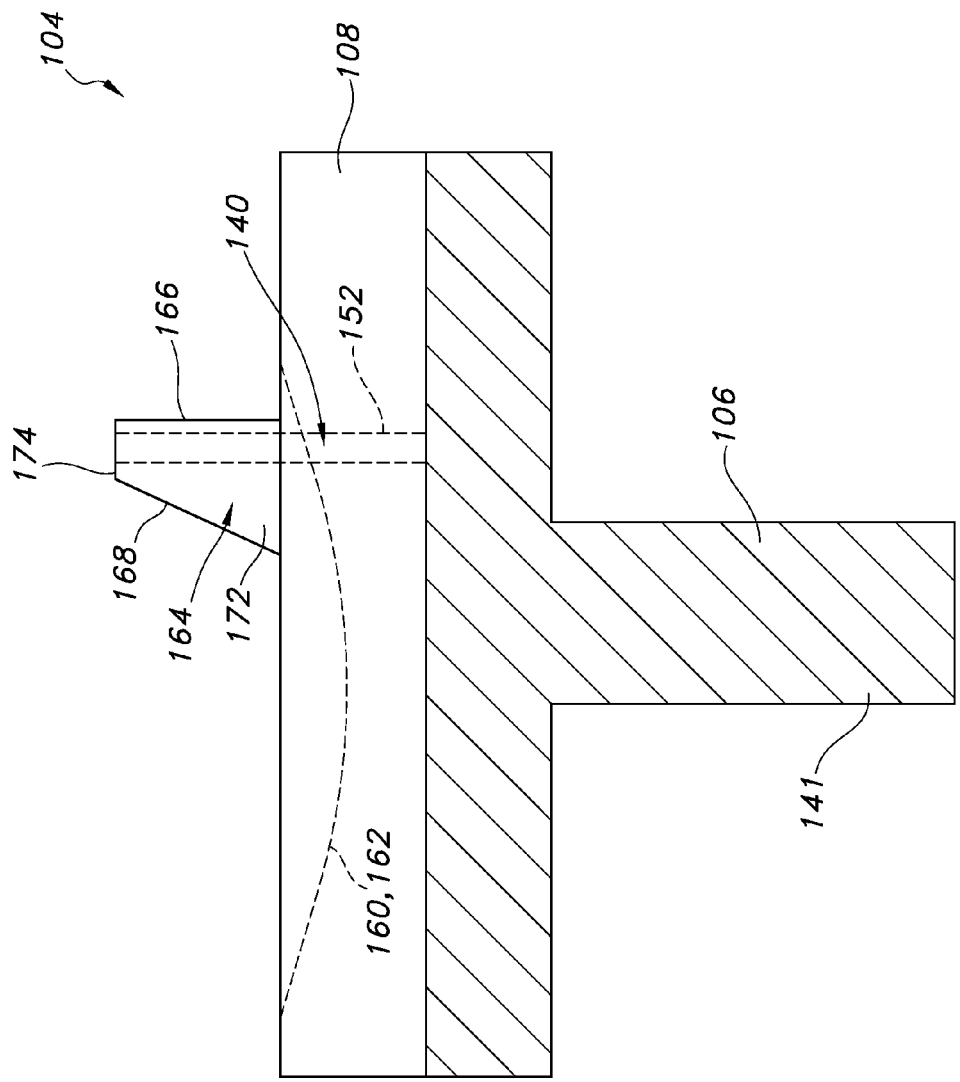
FIG. 9 is a profile view of an exemplary distal component in accordance with the present disclosure.

Referencing FIGS. 4 and 9, the exemplary tibial tray 106 includes a stem 141 that is adapted to be received within the intramedullary canal of the tibia. The stem 141 may be cemented or adapted for bone ingrowth to permanently mount the tibial tray 106 to the tibia. Integral with the stem 141 is a platform 142 on which the tibial tray insert 108 is mounted. In this regard, the tibial tray 106 may provide either a fixed bearing interface to lock the orientation of the tibial tray insert 108 with the tibial tray 106 or a mobile bearing interface that allows the tibial tray insert 108 to move independent of the tibial tray 106.

A first exemplary tibial tray 106 includes a first cylindrical projection 140 that extends upward from the platform 142 in a direction generally perpendicular to the face of the platform. This first cylindrical projection 140 is substantially centered from anterior-to-posterior and lateral-to-medial on the platform 142. In exemplary form, the projection 140 is received within a cavity 152 extending through the tibial tray insert 108, but not received so tightly as to inhibit rotation of the tibial tray insert with respect to the projection. It is the combination of the projection 140 and the cavity 152 that provides mobile bearing functionality for the tibial component 104. As will be obvious to those skilled in the art, the cavity 152 and the projection 140 may be switched so that the platform 142 includes the cavity, while the tray insert 108 includes the projection.

The tibial tray insert 108 also includes concave bearing surfaces 160, 162 that are adapted to receive the medial and lateral condyles 114, 112 of the femoral component 102. The two concave bearing surfaces 160, 162 are partially separated from one another by a trapezoidal post 164 upstanding from the tibial tray insert 108. In this exemplary embodiment, the post 164 is integrally formed with the tibial tray insert 108. However, it is also within the scope of the invention that the post 164 is separable from the tibial tray insert 108 and its location is independent of the location/movement of the tibial tray insert. The post 164 includes an anterior wall 166 having a substantially vertical face and a posterior wall 168 having an inclined face from posterior to anterior. The vertical face of the anterior wall 166 is substantially parallel with the anterior-posterior centerline. The anterior wall 166 and posterior wall 168 are separated from one another by substantially vertical medial and lateral side walls 170, 172 and a horizontal top wall 174.

Figure 10:
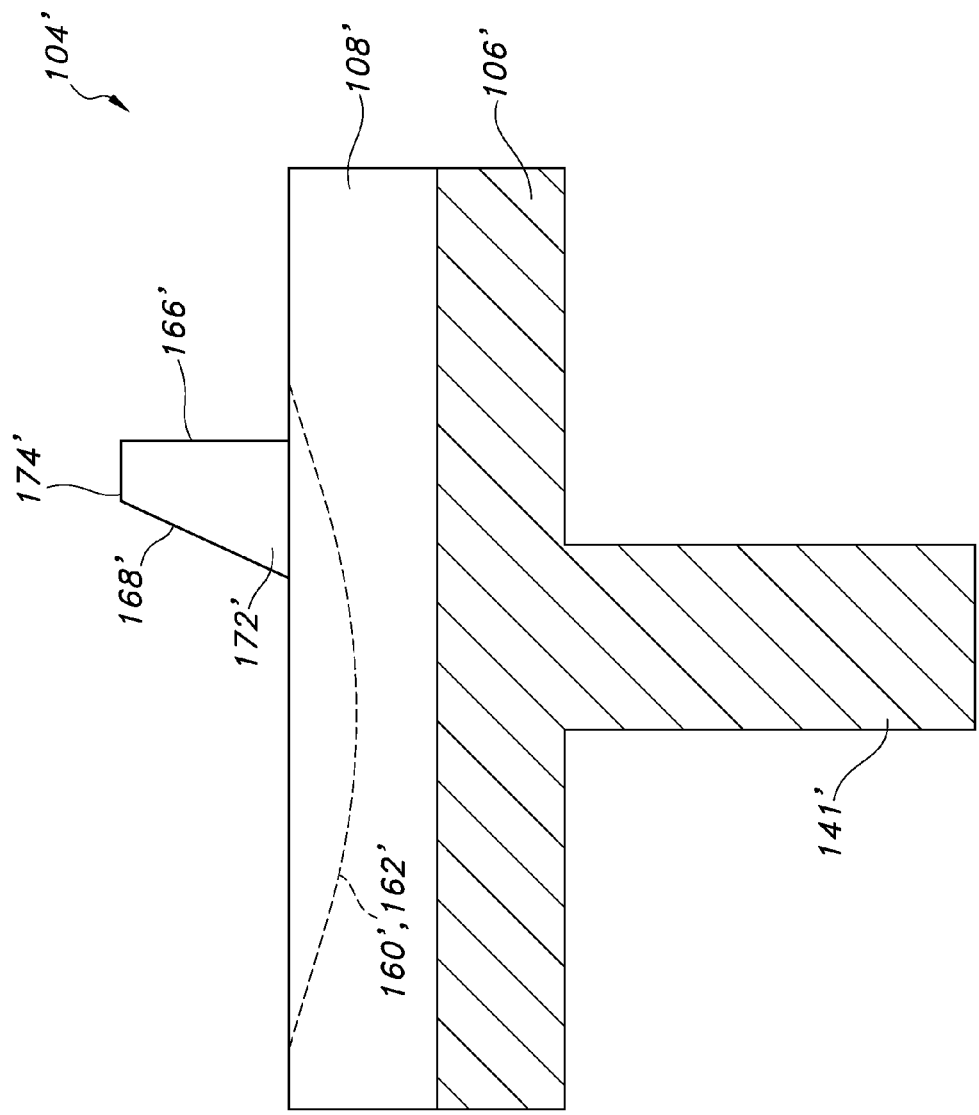
FIG. 10 is a profile view of another exemplary distal component in accordance with the present disclosure.

Referring to FIG. 10, an alternate exemplary fixed bearing tibial component 104' includes a tibial tray 106' and a tibial tray insert 108'. In this exemplary embodiment, the tibial tray 106' includes a stem 141' that is adapted to be received within the intramedullary canal of the tibia. The stem 141' may be cemented or adapted for bone ingrowth to permanently mount the tibial tray 106' to the tibia. Integral with the stem 141' is a platform 142' on which the tibial tray insert 108' is mounted.

The tibial tray insert 108' also includes concave bearing surfaces 160', 162' that are adapted to receive the medial and lateral condyles 114, 112 of the femoral component 102 (see FIG. 4). The two concave bearing surfaces 160', 162' are partially separated from one another by a trapezoidal post 164' upstanding from the tibial tray insert 108'. In this exemplary embodiment, the post 164' is integrally formed with the tibial tray insert 108' and includes an anterior wall 166' having a substantially vertical face and a posterior wall 168' having an inclined face from posterior to anterior. The vertical face of the anterior wall 166' is substantially parallel with the anterior-posterior centerline. The anterior wall 166' and posterior wall 168' are separated from one another by substantially vertical medial and lateral side walls 170', 172' and a horizontal top wall 174'.

Figure 11:
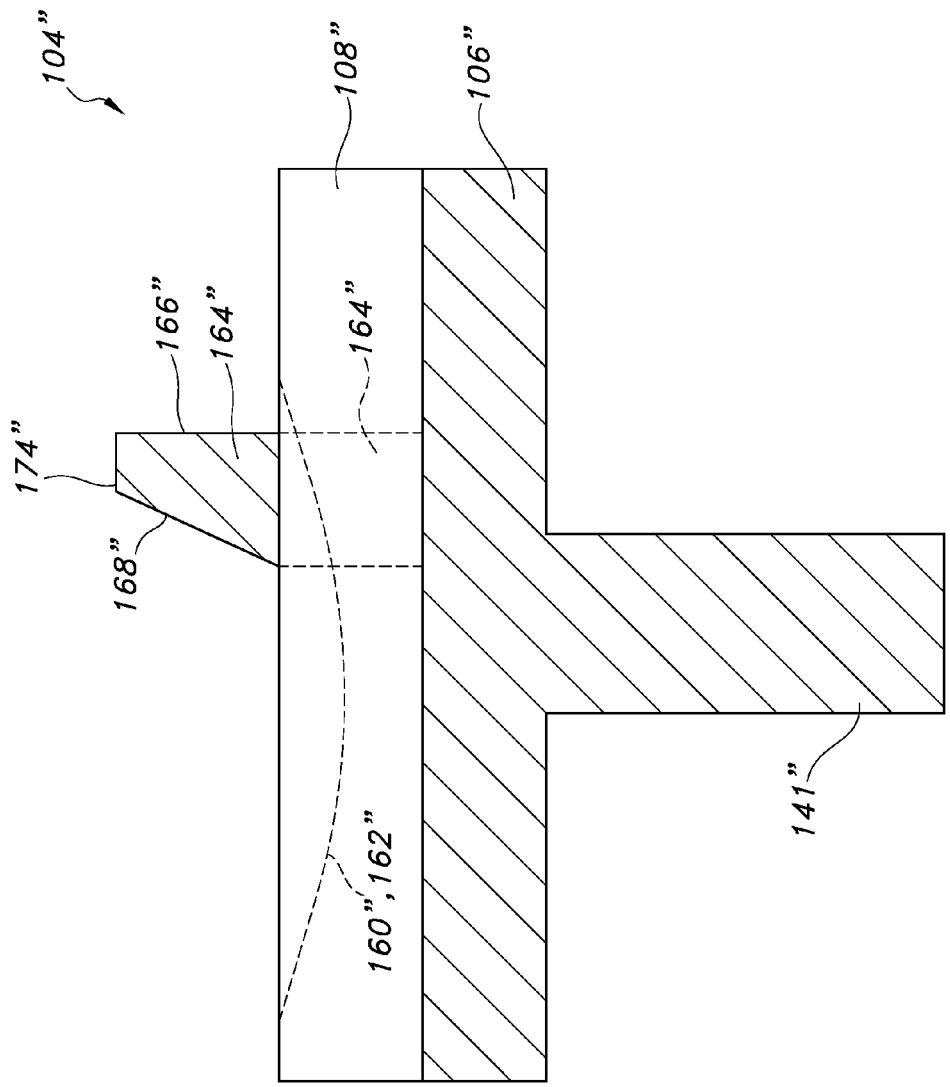
FIG. 11 is a profile view of a further exemplary distal component in accordance with the present disclosure.

Referring to FIG. 11, a further alternate exemplary fixed bearing tibial component 104" includes a tibial tray 106" and a tibial tray insert 108". In this exemplary embodiment, the tibial tray 106" includes a stem 141" that is adapted to be received within the intramedullary canal of the tibia. The stem 141" may be cemented or adapted for bone ingrowth to permanently mount the tibial tray 106" to the tibia. Integral with the stem 141" is a platform 142" on which the tibial tray insert 108" is mounted.

The tibial tray insert 108" also includes concave bearing surfaces 160", 162" that are adapted to receive the medial and lateral condyles 114, 112 of the femoral component 102 (see FIG. 4). The two concave bearing surfaces 160", 162" are partially separated from one another by a trapezoidal post 164" upstanding from the tibial tray insert 108". In this exemplary embodiment, the post 164" is integrally formed with the tibial tray 106". However, it is also within the scope of the invention that the post 164" is separable from the tibial tray 106" and correspondingly its location is not dependent upon the variable location of a mobile bearing tibial tray. The post 164" includes an arcuate anterior wall 166" having a substantially vertical face and a posterior conical wall 168" having an arcuate, inclined face from posterior to anterior. The anterior wall 166" and posterior wall 168" are joined seamlessly to one another and transition at the top to a flat, substantially horizontal top wall 174".

Figure 12:
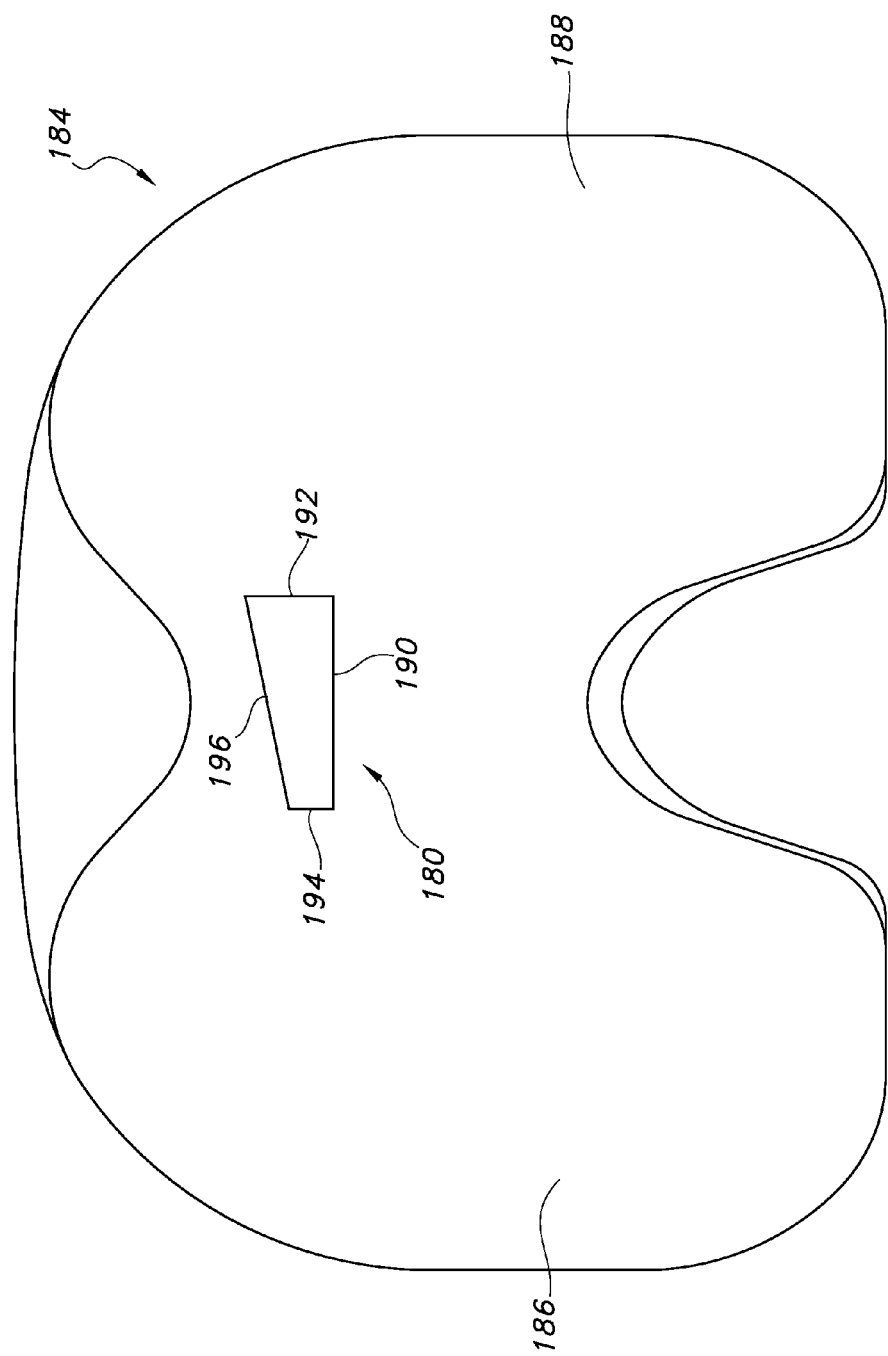
FIG. 12 is a top view of an exemplary tibial tray insert in accordance with the present disclosure.
Figure 13:
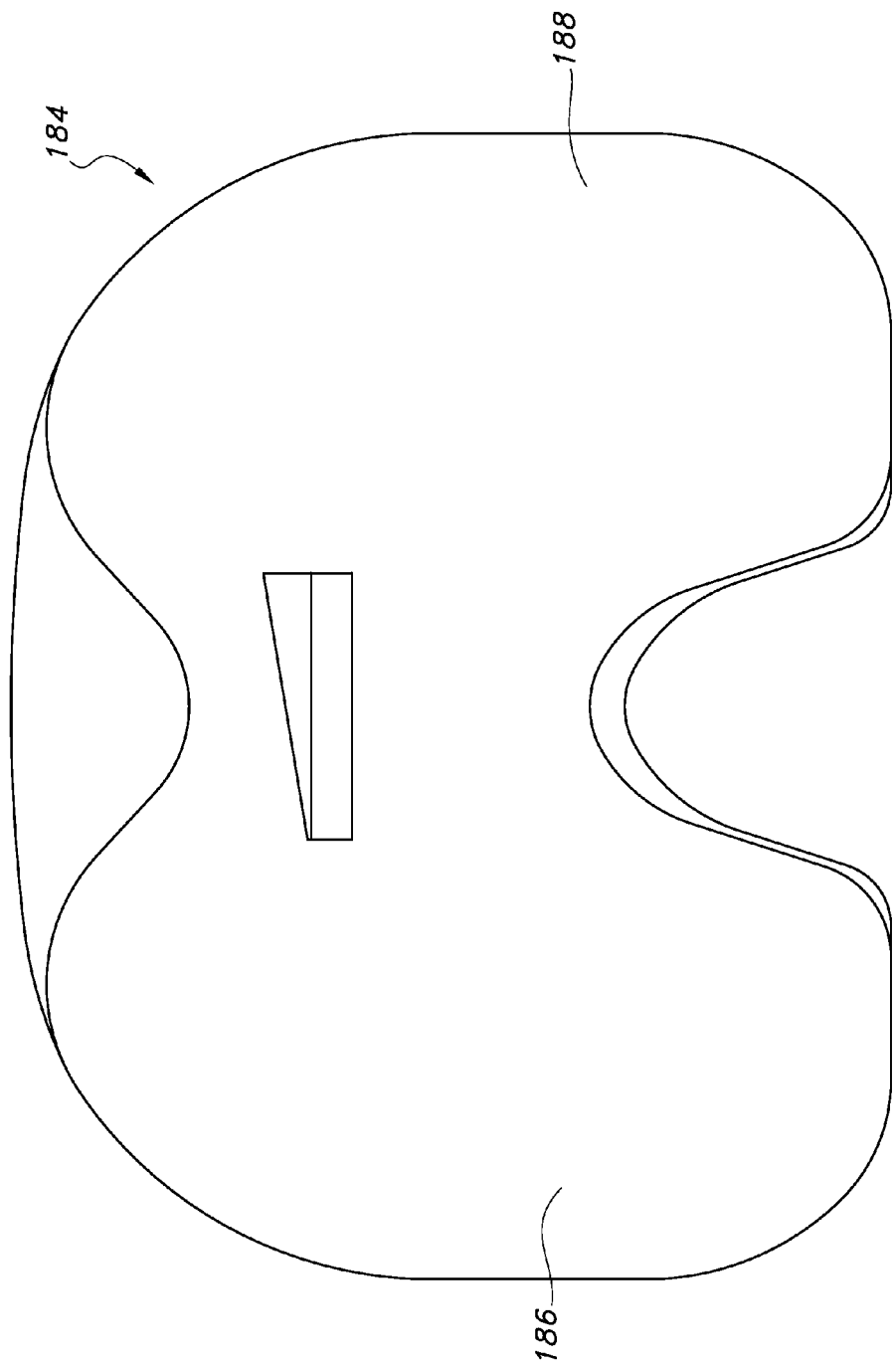
FIG. 13 is a top view of another exemplary tibial tray insert in accordance with the present disclosure.

Referencing FIGS. 12 and 13, an alternate exemplary tibial tray insert 184 for use in combination with the exemplary femoral components 102 includes a tibial post 180, 182 and adjacent medial and lateral condyles 186, 188. The exemplary tibial post 180, 182, in contrast to the foregoing exemplary tibial posts 164, includes an anterior wall angled other than parallel with respect to the anterior-posterior centerline to the tibial tray insert 184.

Referring to FIG. 12, a first exemplary post 180 includes a generally trapezoidal shape exposed portion above the surface of the tibial tray insert 184. The post comprises a flat, substantially vertical posterior surface 190 and flat, substantially vertical side surfaces 192, 194. An anterior surface 196 is flat and substantially vertical, but is angled 20 degrees with respect to the anterior-posterior centerline. In other words, the leading or anterior edge on the lateral side of the post 180 is closer to the front of the tibial tray insert 184 than is the leading or anterior edge on the medial side of the post. In this manner, as the camming surface of the femoral component contacts the anterior face of the post 180, the angle of the anterior surface cause the femoral component to rotate medially.

Referring to FIG. 13, a second exemplary post 182 includes a generally trapezoidal shape exposed portion above the surface of the tibial tray insert 184. The post comprises a flat, substantially vertical posterior surface 200 and flat, substantially vertical side surfaces 202, 204. An anterior surface 206 is inclined from anterior-to-posterior and angled with respect to the anterior-posterior centerline of the tibial tray insert 184. In this exemplary embodiment, the anterior surface is angled 20 degrees with respect to the anterior-posterior centerline and angled 70 degrees with respect to horizontal. In other words, the bottom corner of the anterior surface and the lateral side 188 is closer to the front of the tibial tray insert 184 than is the bottom corner of the anterior edge on the medial side of the post 182. In this manner, as the camming surface of the femoral component contacts the anterior face of the post 180, the angle and decline of the anterior surface cause the femoral component to rotate medially.

Figure 14:
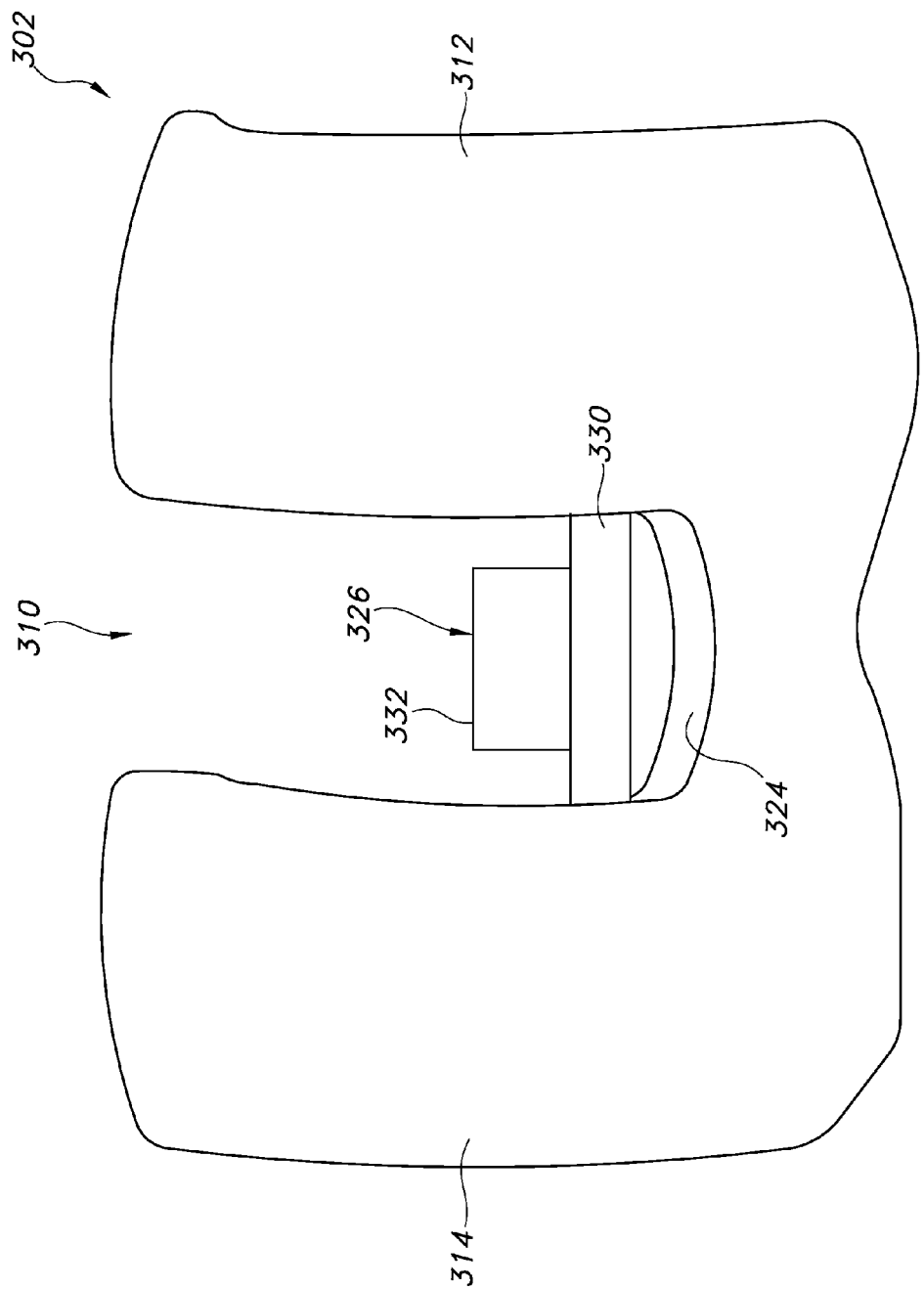
FIG. 14 is a bottom view of still a further exemplary femoral component in accordance with the present disclosure.
Figure 15:
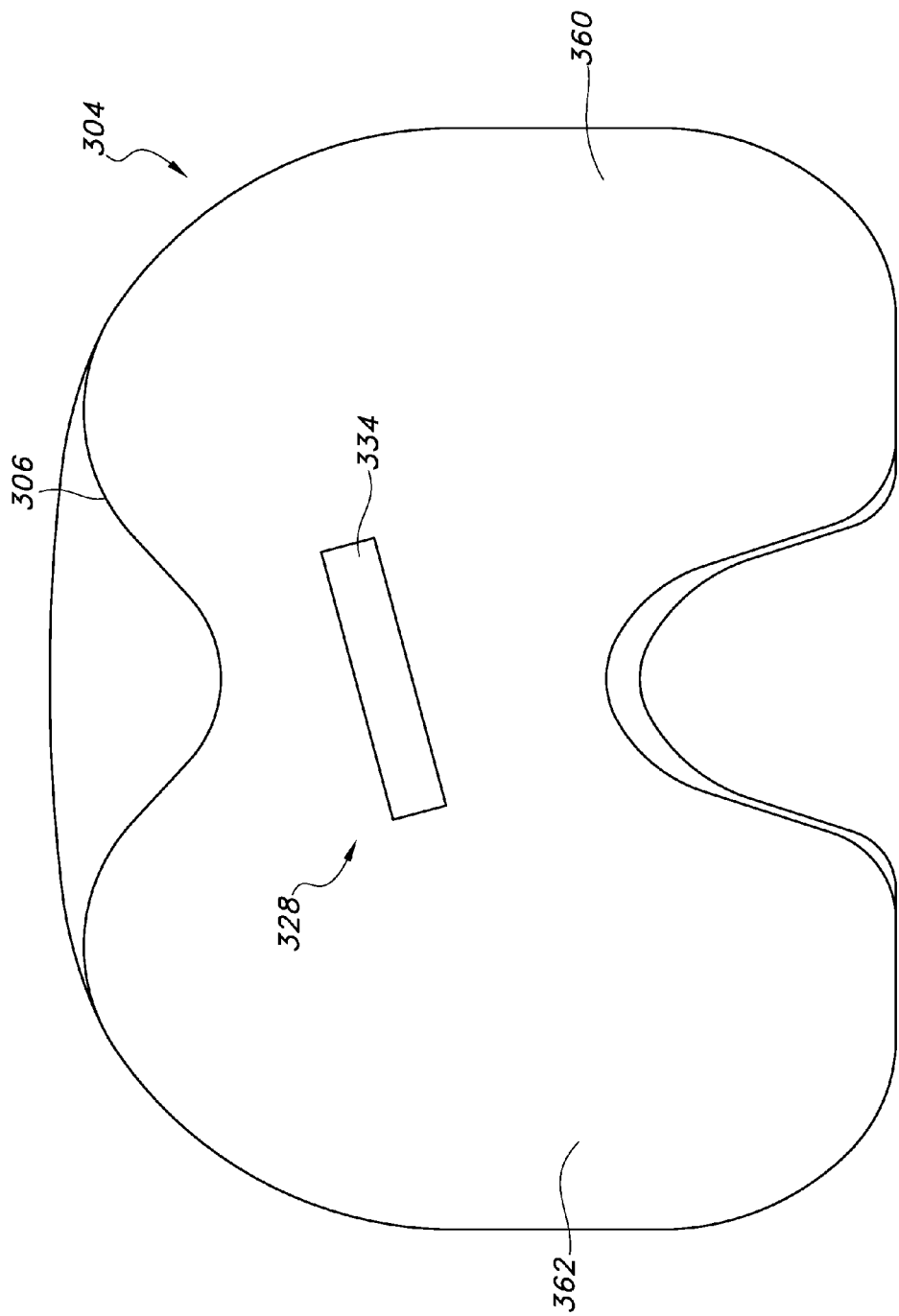
FIG. 15 is a top view of another exemplary femoral tibial tray insert in accordance with the present disclosure.
Figure 16:
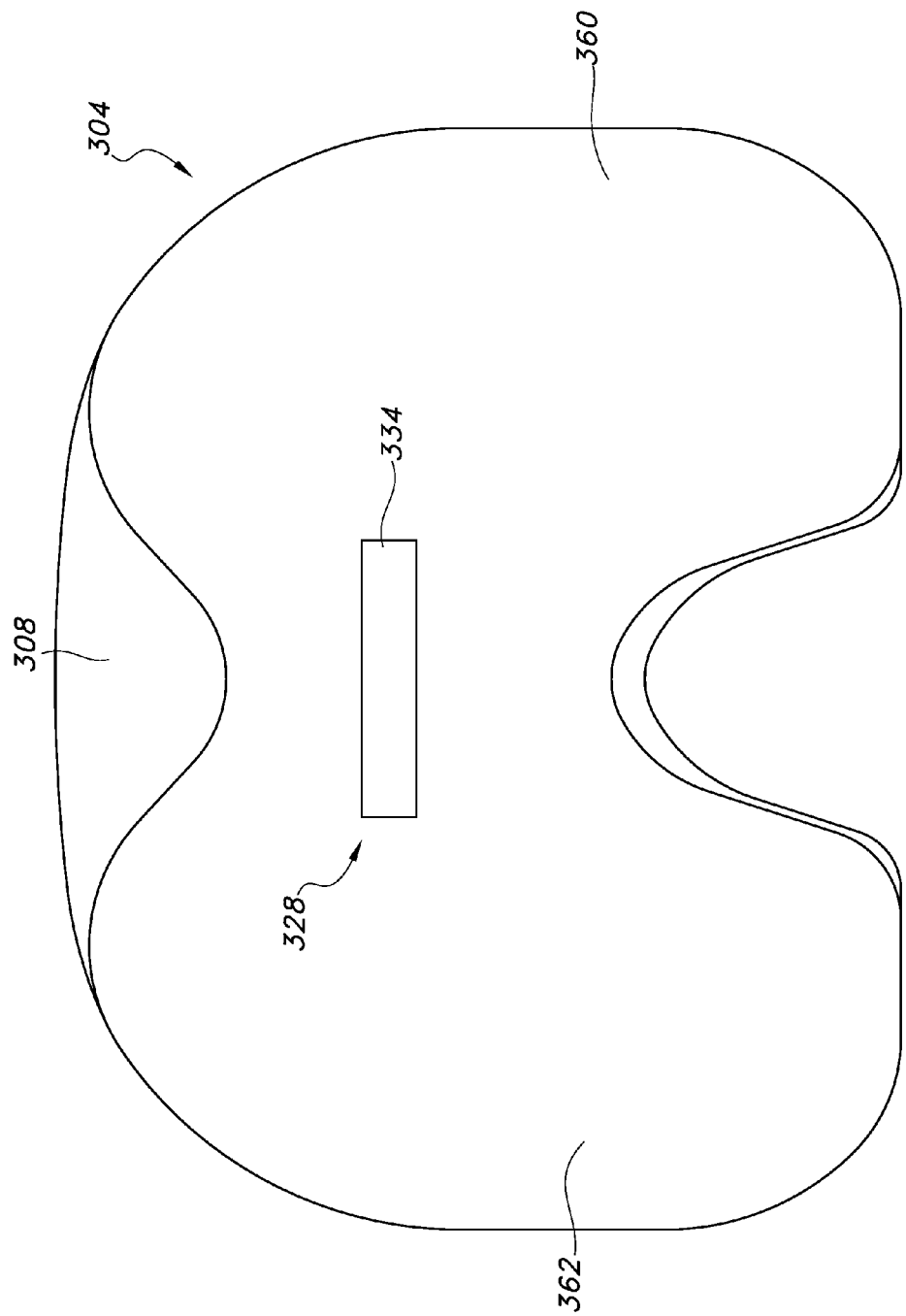
FIG. 16 is a top view of yet another exemplary tibial tray insert in accordance with the present disclosure.

Referring to FIGS. 14-16, a second exemplary posterior cruciate retaining orthopedic knee implant for use with total arthroplasty procedures includes a femoral component 302 and a tibial component 304. In this exemplary embodiment, the tibial component 304 comprises a tibial tray (not shown) and a tibial tray insert 306, 308.

The exemplary posterior cruciate retaining orthopedic femoral component 302 include a posterior discontinuity or gap 310 between lateral and medial condyles 312, 314 to allow the femoral component to rotate between maximum extension and maximum flexion without impinging the posterior cruciate ligament, which is retained. Those skilled in the art are familiar with the posterior constraint resulting from retention of the posterior cruciate ligament, whereas those skilled in the art are also familiar with the absence of anterior constraint resulting from the absence of the anterior cruciate ligament.

Referring specifically to FIG. 14, this exemplary femoral component 302 includes two condyles 312, 314 each having an arcuate shape in order to allow for smooth rotation of the femur with respect to the tibia. As the shape of the condyles 312, 314 becomes more pronounced, the condyles separate from one another, which is marked by an arcuate bridge 324 formed at the most proximal connection point of the condyles. As the shape of the condyles 312, 314 continues distally, past the arcuate bridge 324, the condyles widen and generally flare out on the outer edges. At the same time, the bearing surfaces of the condyles 312, 314 flatten out and do not exhibit a uniform arcuate shape from anterior to posterior. However, the posterior discontinuity or gap 310 has a substantially uniform width, resulting in the inner shape and contour of the condyles being substantially the same. Unlike prior art posterior cruciate retaining femoral components, the exemplary posterior cruciate retaining femoral component 302 includes an anterior post 326 that engages a tibial cam 328 of the tibial component 304.

The anterior femoral post 326 of the femoral component 302 is mounted to a recessed bracket 330 extending between the condyles 312, 314 proximate the bridge 324. In exemplary form, the femoral post 326 includes a rectangular cross-section and a sloped posterior face 332.

Referring to FIG. 15, the tibial component 304 may include a first exemplary tibial tray insert 306 having concave bearing surfaces 360, 362 that are adapted to receive the medial and lateral condyles 314, 312 of the femoral component 302. The two concave bearing surfaces 360, 362 are partially separated from one another by the tibial cam 328 upstanding from the tibial tray insert 306. In this exemplary embodiment, the cam 328 is integrally formed with the tibial tray insert 306. However, it is also within the scope of the invention that the cam 328 is separable from the tibial tray insert 306 and correspondingly moves independent of the tibial tray insert. The cam 328 includes a rounded exterior surface 334, which is angled other than perpendicular with respect to the anterior-posterior centerline. In this exemplary embodiment, the cam 328 is angled at 20 degrees with respect to the anterior-posterior centerline.

Referring to FIG. 16, the tibial component 304 may include a second exemplary tibial tray insert 308 having concave bearing surfaces 360, 362 that are adapted to receive the medial and lateral condyles 314, 312 of the femoral component 302. The two concave bearing surfaces 360, 362 are partially separated from one another by the tibial cam 328 upstanding from the tibial tray insert 306. In this exemplary embodiment, the cam 328 is integrally formed with the tibial tray insert 306. However, it is also within the scope of the invention that the cam 328 is separable from the tibial tray insert 306 and correspondingly moves independent of the tibial tray insert. The cam 328 includes a rounded exterior surface 334, which is perpendicularly angled with respect to the anterior-posterior centerline.

In operation, the femoral post 326 and tibial cam 328 work together to anteriorly stabilize the orthopedic knee replacement joint. Presuming a range of motion starting at fully flexion, the condyles 312, 314 of the femoral component 302 rotate from posterior to anterior so that eventually the posterior face 332 of the post 326 engages the anterior rounded exterior surface 334 of the femoral cam 328 to anteriorly stabilize the knee joint at near full extension up through full extension. When the femoral component 302 is rotated from anterior to posterior from full extension toward full flexion, the femoral post 326 gradually disengages against the tibial cam 326 so that posterior stability is provided by the retained posterior cruciate ligament at near full flexion toward full flexion.

In the circumstance where the femoral post 326 is angled toward the medial condyle 362, presuming a range of motion starting at fully flexion, the condyles 312, 314 of the femoral component 302 rotate from posterior to anterior so that eventually the posterior face 332 of the post 326 engages the anterior rounded exterior surface 334 of the femoral cam 328 on the lateral side and rotates the femoral component 302 medially combined with anterior stabilization the knee joint at near full extension up through full extension. Continued extension beyond initial engagement between the femoral post 326 and the tibial cam 328 results in more pronounced rotation so that eventually the femoral post 326 rides square upon the tibial cam 328 at maximum extension. When the femoral component 302 is rotated from anterior to posterior from full extension toward full flexion, the femoral post 326 gradually disengages against the tibial cam 326 combined with lateral rotation of the femoral component 302 so that posterior stability is provided by the retained posterior cruciate ligament at near full flexion toward full flexion.

Figure 17:
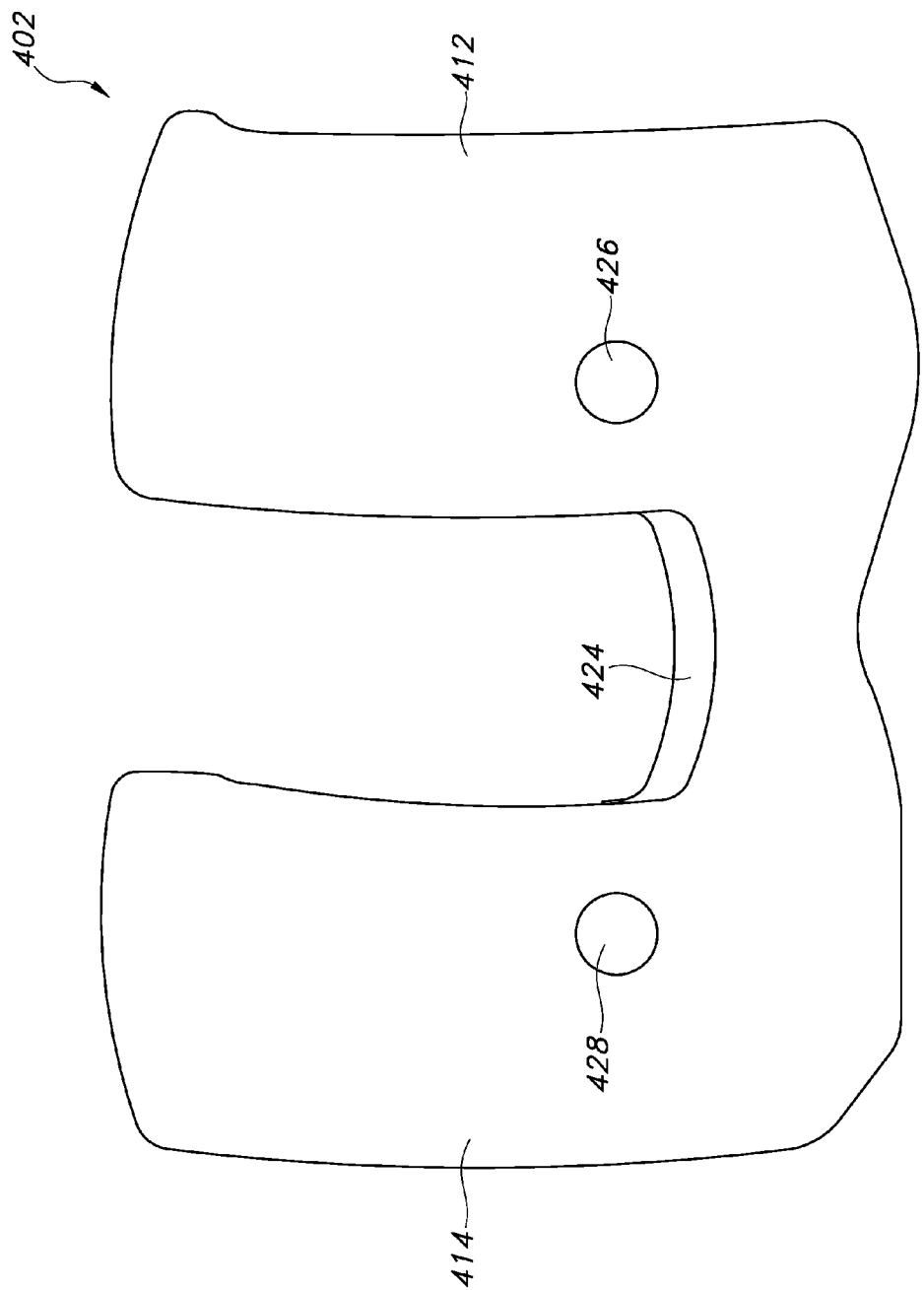
FIG. 17 is a bottom view of another exemplary femoral component in accordance with the present disclosure.
Figure 18:
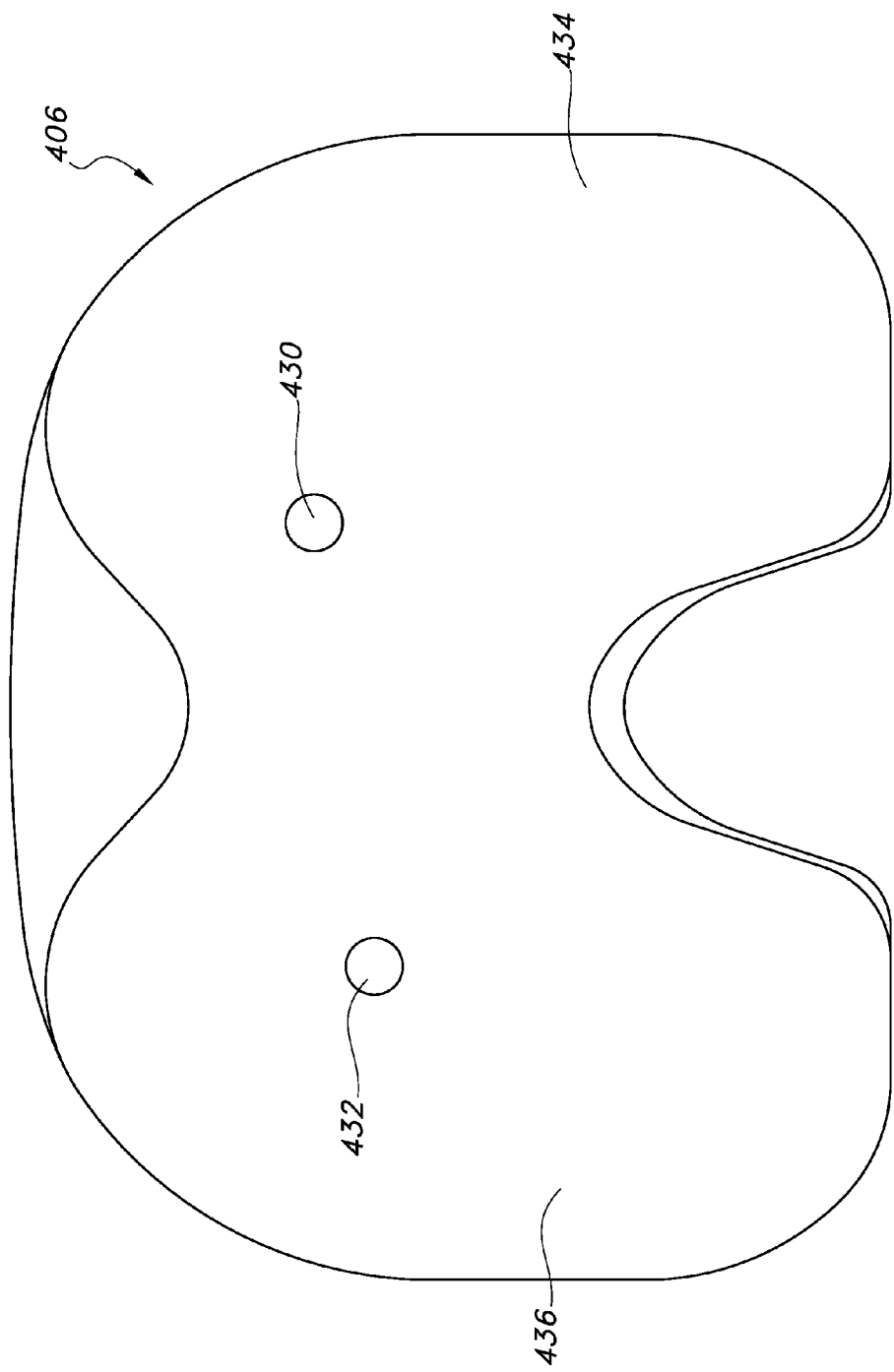
FIG. 18 is a top view of still a further exemplary tibial tray insert in accordance with the present disclosure.

Referring to FIGS. 17 and 18, a third exemplary posterior cruciate retaining orthopedic knee implant for use with total arthroplasty procedures includes a femoral component 402 and a tibial component (not totally shown). In this exemplary embodiment, the tibial component comprises a tibial tray (not shown) and a tibial tray insert 406. The exemplary posterior cruciate retaining orthopedic femoral component 402 include a posterior discontinuity or gap 410 between lateral and medial condyles 412, 414 to allow the femoral component to rotate between maximum extension and maximum flexion without impinging the posterior cruciate ligament, which is retained. Those skilled in the art are familiar with the posterior constraint resulting from retention of the posterior cruciate ligament, whereas those skilled in the art are also familiar with the absence of anterior constraint resulting from the absence of the anterior cruciate ligament.

Referring specifically to FIG. 17, this exemplary femoral component 402 includes two condyles 412, 414 each having an arcuate shape in order to allow for smooth rotation of the femur with respect to the tibia. As the shape of the condyles 412, 414 becomes more pronounced, the condyles separate from one another, which is marked by an arcuate bridge 424 formed at the most proximal connection point of the condyles. As the shape of the condyles 412, 414 continues distally, past the arcuate bridge 424, the condyles widen and generally flare out on the outer edges. At the same time, the bearing surfaces of the condyles 412, 414 flatten out and do not exhibit a uniform arcuate shape from anterior to posterior. However, unlike prior art posterior cruciate retaining femoral components, the exemplary posterior cruciate retaining femoral component 402 includes a lateral condyle cylindrical projection 426 and a medial condyle cylindrical projection 428.

Referring to FIG. 18, the tibial tray insert 406 includes lateral and medial condyle receivers 434, 436 that are adapted to receive the lateral and medial condyles 412, 414 of the femoral component 402. In exemplary form, each of the condyle receivers includes a corresponding cavity 430, 432 adapted to receive the condyle projections 426, 428 of the femoral component.

In operation, the femoral projections 426, 428 and tibial cavities 430, 432 work together to anteriorly stabilize the orthopedic knee replacement joint. Presuming a range of motion starting at fully flexion, the condyles 412, 414 of the femoral component 402 rotate from posterior to anterior so that eventually the lateral projection 426 on the lateral condyle 412 engages the lateral cavity 430 in the lateral condyle receiver 434 to inhibit sliding of the lateral condyle with respect to the lateral condyle receiver. Continued rotation 334 of the femoral component 402 with respect to the tibial tray insert 406 causes the femoral component to pivot about the lateral condyle receiver cavity 430 so that the femoral component rotates medially until the medial condyle projection 428 is received within the medial condyle cavity 432. The corresponding inhabitation of sliding as the femoral component 402 is rotated provides anterior stability as the knee joint is near full extension through full extension. Conversely, as the femoral component 402 is rotated from anterior to posterior from full extension toward full flexion, the femoral condyle projections 426, 428 disengage from the cavities 430 432 of the tibial tray insert 406 so that posterior stability is provided by the retained posterior cruciate ligament at near full flexion toward full flexion.

Figure 19:
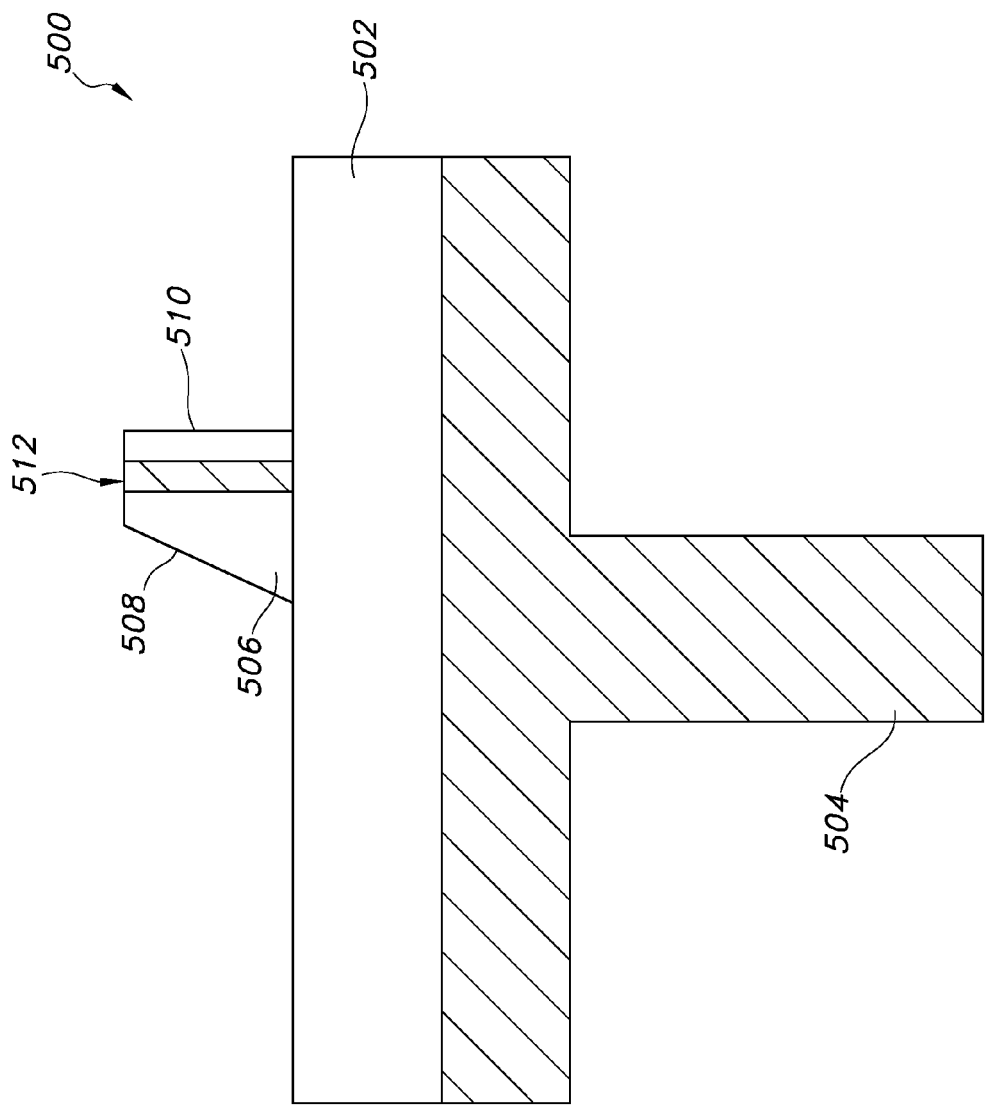
FIG. 19 is a profile view of an exemplary tibial component in accordance with the present disclosure.

Referring to FIG. 19, an exemplary tibial component 500 includes a tibial tray insert 502 mounted to a tibial tray 504. In this exemplary tibial component, an anterior post 506 is mounted to either the tibial tray insert 502 or the tibial tray 504 so that an anterior cam of a femoral component (not shown) engages the post to pull the femur anterior with respect to the tibia. The exemplary post 506 includes a posterior aspect 508 and an anterior aspect 510 that are interposed by a resilient material or one or more springs 512. In this exemplary embodiment, the post 506 includes a pair of springs 512, one on the medial side and one on the lateral side. More specifically, the spring rate of the medial spring is less than the spring rate of the lateral spring so that contact with the anterior cam of the femoral component is operative to push the anterior aspect 510 on the medial side more posterior than the lateral side of the anterior aspect. It is to be understood, however, that only one or more than two springs may be utilized. In addition, when multiple springs are utilized, the spring rates may be uniform or varied. In addition or in lieu of springs, resilient materials may be utilized that have different compression ratings or the same material may be utilized. Those skilled in the art will understand the plethora of options available by using a resilient material or a spring to interpose the anterior and posterior aspects of the tibial post.

The exemplary femoral components of the exemplary embodiments may be fabricated from a hard and durable biocompatible material such as a titanium alloy, cobalt chrome alloy, alumina ceramic or zirconia ceramic. However, those of skill in the art will appreciate that any material can be used for this or the other components of a total knee implant while remaining within the scope of the present invention.

The exemplary tibial components may be fabricated from a biocompatible material such as, without limitation, polyethylene, ultra high molecular weight polyethylene, highly cross-linked ultra high molecular weight polyethylene, a ceramic, and any biocompatible metal.

While the foregoing exemplary embodiments have been described to have a separable tibial tray and a tibial tray insert, it is to be understood that the tibial tray may include condyle receiver bearing surfaces that obviate the need for a separate tibial tray insert.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A total knee implant prosthesis comprising:
a posterior ligament retaining femoral component including a pair of condyles interposed by an opening, the femoral component also including an anterior cam and being free from any posterior cam, the anterior cam extending between the condyles adjacent to the opening; and
a posterior ligament retaining tibial component, the tibial component including a post and a pair of condyle depressions;
wherein:
the post extends upwardly from between the condyle depressions and includes an anterior surface;
the anterior cam and post are sized, shaped and positioned so that the anterior cam and the anterior surface of the post are engaged when the knee is fully extended and the anterior cam and the anterior surface of the post are disengaged during at least part of flexion of the knee.

2. The total knee implant prosthesis of claim 1, wherein the posterior ligament retaining tibial component includes a tibial tray and a tibial tray insert.

3. The total knee implant prosthesis of claim 2, wherein the tibial tray insert is a mobile bearing insert.

4. The total knee implant prosthesis of claim 2, wherein the tibial tray insert is a fixed bearing insert.

5. The total knee implant prosthesis of claim 2, wherein:
the tibial tray insert includes the pair of condyle depressions; and
the tibial tray includes the post.

6. The total knee implant prosthesis of claim 2, wherein:
the tibial tray insert includes the pair of condyle depressions; and
the tibial tray insert includes the post.

7. The total knee implant prosthesis of claim 2, wherein the post is separable from both the tibial tray insert and the tibial tray.

8. The total knee implant prosthesis of claim 7, wherein:
at least one of the tibial tray and the tibial tray insert includes a projection; and
the post includes a plurality of cavities, each of the plurality of cavities sized to separately accommodate at least a portion of the projection to secure the post to at least one of the tibial tray and the tibial tray insert.

9. The total knee implant prosthesis of claim 7, wherein:
the post includes a projection; and
at least one of the tibial tray and the tibial tray insert includes a plurality of cavities, each of the plurality of cavities adapted to house a portion of the projection to secure the post to at least one of the tibial tray and the tibial tray insert.

10. The total knee implant prosthesis of claim 7, wherein the anterior cam is at least one of inset with respect to the medial and lateral condyles, flush with respect to the medial and lateral condyles, and projects outward with respect to the medial and lateral condyles.

11. The total knee implant prosthesis of claim 2, wherein:
the tibial tray insert comprises independent pieces;
a first independent piece includes a medial condyle depression of the pair of condyle depressions; and
a second independent piece includes a lateral condyle depression of the pair of condyle depressions;
wherein at least one of the first independent piece and the second independent piece is mobile bearing with respect to the tibial tray.

12. The total knee implant prosthesis of claim 1, wherein the anterior cam is mobile bearing with respect to at least one of the pair of condyles.

13. The total knee implant prosthesis of claim 1, wherein the anterior cam is fixed bearing with respect to the pair of condyles.

14. The total knee implant prosthesis of claim 1, wherein an anterior surface of the post is planar and substantially vertical.

15. The total knee implant prosthesis of claim 1, wherein an anterior surface of the post is sloped upward from anterior to posterior.

16. The total knee implant prosthesis of claim 1, wherein an anterior surface of the post is substantially planar and angled to face toward a first of the pair of condyle depressions and away from a second of the pair of condyle depressions.

17. The total knee implant prosthesis of claim 1, wherein an anterior surface of the post includes a helical groove.

18. The total knee implant prosthesis of claim 17, wherein an anterior surface includes a projection to be received within the helical groove in the post.

19. The total knee implant prosthesis of claim 1, wherein an anterior surface of the post includes a helical projection.

20. The total knee implant prosthesis of claim 19, wherein the helical projection is at least one of symmetrical and asymmetrical.

21. The total knee implant prosthesis of claim 20, wherein the helical projection is asymmetrical and a lateral portion of the helical projection protrudes outward on a lateral side more than on a medial side.

22. The total knee implant prosthesis of claim 1, wherein an anterior surface of the post is sloped upward from posterior to anterior.

23. The total knee implant prosthesis of claim 1, wherein an anterior surface of the anterior cam is rounded and substantially perpendicularly oriented with respect to the pair of condyles.

24. The total knee implant prosthesis of claim 1, wherein an anterior surface of the anterior cam is planar and angled to face toward a first of the pair of condyles and away from a second of the pair of condyles.

25. The total knee implant prosthesis of claim 1, wherein an anterior surface of the anterior cam is planar and substantially perpendicularly oriented with respect to the pair of condyles.

26. The total knee implant prosthesis of claim 1, wherein an anterior surface of the anterior cam is rounded and angled to face toward a first of the pair of condyles and away from a second of the pair of condyles.

27. The total knee implant prosthesis of claim 1, wherein an anterior surface of the anterior cam includes a helical projection.

28. The total knee implant prosthesis of claim 27, wherein the helical projection is at least one of symmetrical and asymmetrical.

29. The total knee implant prosthesis of claim 1, wherein the post includes a base having a cross-section larger than a cross-section at a top of the post farthest from the tibial tray.

30. The total knee implant prosthesis of claim 1, wherein:
the tibial tray includes a projection that extends into an area bounded by the tibial tray insert; and
the post is mounted to the projection.

31. The total knee implant prosthesis of claim 30, wherein the post is fixed bearing with respect to the projection.

32. The total knee implant prosthesis of claim 1, wherein post is between 0.125 millimeters and 50 millimeters in length from anterior to posterior.

33. The total knee implant prosthesis of claim 1, wherein post is between 0.125 millimeters and 50 millimeters in width from medial to lateral.

34. The total knee implant prosthesis of claim 1, wherein post is between 0.125 millimeters and 50 millimeters in height from superior to inferior.

35. The total knee implant prosthesis of claim 1, wherein the anterior cam is resilient.

36. The total knee implant prosthesis of claim 1, wherein the anterior cam includes a shock absorber.

37. The total knee implant prosthesis of claim 1, wherein the anterior cam includes a spring.

38. The total knee implant prosthesis of claim 1, wherein the anterior cam includes at least two springs, where at least two of the springs have symmetrical spring coefficient.

39. The total knee implant prosthesis of claim 1, wherein the anterior cam includes at least a medial spring and a lateral spring, where the medial spring and the lateral spring have asymmetrical spring rates.

40. The total knee implant prosthesis of claim 39, wherein a spring rate of the medial spring is lower than a spring rate of the lateral spring.

41. The total knee implant prosthesis of claim 1, wherein the post is resilient.

42. The total knee implant prosthesis of claim 1, wherein the post includes a shock absorber.

43. The total knee implant prosthesis of claim 1, wherein the post includes a spring.

44. The total knee implant prosthesis of claim 1, wherein the post includes at least two springs, where at least two of the springs have symmetrical spring coefficient.

45. The total knee implant prosthesis of claim 1, wherein the post includes at least a medial spring and a lateral spring, where the medial spring and the lateral spring have asymmetrical spring rates.

46. The total knee implant prosthesis of claim 45, wherein a spring rate of the medial spring is lower than a spring rate of the lateral spring.

47. The total knee implant prosthesis of claim 1, wherein:
the femoral component includes a projection; and
the anterior cam includes a plurality of cavities, each of the plurality of cavities sized to separately accommodate at least a portion of the projection to secure the anterior cam to the femoral component.

48. The total knee implant prosthesis of claim 1, wherein:
the anterior cam includes a projection; and
the femoral component includes a plurality of cavities, each of the plurality of cavities sized to separately accommodate at least a portion of the projection to secure the anterior cam to the femoral component.

49. The knee implant prosthesis of claim 1, wherein the post engages the anterior cam at between 0 to about 50 degrees of joint flexion.

50. The knee implant of claim 1, wherein the anterior cam and post combination results in up to 25 degrees of axial rotation between the femoral and the bearing component.

51. The knee implant of claim 1, wherein:
the condyles are joined by a bridge at a position spaced from the anterior cam; and
the condyles are free from any connection between them between the anterior cam and the bridge.

52. The knee implant of claim 51 wherein the condyles have posterior ends and the opening extends from the anterior cam to the posterior ends of the condyles so that the condyles are free from any connection between them between the anterior cam and the posterior ends of the condyles.

53. A total knee implant prosthesis comprising:
a posterior ligament retaining femoral component including a pair of condyles interposed by an opening, the femoral component also including an anterior cam and being free from any posterior cam; and
a posterior ligament retaining tibial component, the tibial component including a post and a pair of condyle depressions;
wherein:
an anterior surface of the anterior cam includes a helical projection;
the helical projection is at least one of symmetrical and asymmetrical; and
the helical projection is asymmetrical and a lateral portion of the helical projection protrudes outward on a lateral side more than on a medial side.

* * * * *